(12) United States Patent
Abbasi

US011648037B2

(10) Patent No.: US 11,648,037 B2
(45) Date of Patent: May 16, 2023

(54) EXTENSION-READY SPINAL SUPPORT SYSTEM WITH VASCULAR-SAFE PEDICLE SCREW

(71) Applicant: Advance Research System, LLC, Edina, MN (US)

(72) Inventor: Hamid R. Abbasi, Edina, MN (US)

(73) Assignee: Advance Research System, LLC, Edina, MN (US)

( * ) Notice: Subject to any disclaimer, the term of this patent is extended or adjusted under 35 U.S.C. 154(b) by 747 days.

(21) Appl. No.: 16/673,521

(22) Filed: Nov. 4, 2019

(65) Prior Publication Data

US 2020/0069341 A1     Mar. 5, 2020

Related U.S. Application Data

(63) Continuation-in-part of application No. 15/970,368, filed on May 3, 2018, now Pat. No. 10,646,260, and
(Continued)

(51) Int. Cl.
*A61B 17/70*     (2006.01)
*A61B 17/86*     (2006.01)
*A61B 17/00*     (2006.01)

(52) U.S. Cl.
CPC ........ *A61B 17/7032* (2013.01); *A61B 17/863* (2013.01); *A61B 17/8635* (2013.01); *A61B 17/7035* (2013.01); *A61B 2017/00858* (2013.01)

(58) Field of Classification Search
CPC .............. A61B 17/7032; A61B 17/863; A61B 17/8635; A61B 17/7035; A61B 2017/00858
(Continued)

(56) References Cited

U.S. PATENT DOCUMENTS 5,261,912 A    11/1993   Frigg
5,520,690 A    5/1996   Errico et al.
(Continued)

FOREIGN PATENT DOCUMENTS

KR   10-2010-0119303    11/2010
WO   WO2010028287     3/2010
(Continued)

OTHER PUBLICATIONS

International Search Report for Application No. PCT/US2018/030928 dated Sep. 27, 2018 (3 pages).

*Primary Examiner* — Ellen C Hammond
*Assistant Examiner* — David C Comstock
(74) *Attorney, Agent, or Firm* — Christensen, Fonder, Dardi & Herbert PLLC; Stuart J. Olstad

(57) ABSTRACT

A "vascular-safe" pedicle screw and extension-ready spinal support system. The pedicle screw includes a self-tapping flute that recessed into a threaded shaft to define terminations of the threads at a face of said self-tapping flute. The terminations are curved to define a convex profile that extends from a root to a crest of the threads at said face of said self-tapping flute. The curved terminations tend to push soft tissue aside as opposed to slicing or tearing through the soft tissue, so that the self-tapping flute is less likely to slice into vascular vessels. The distal portion of the pedicle screw may also include depressions that reduce the circumferential contact area of the pedicle screw in the direction of rotation, which increases the applied pressure to the soft tissue for a given applied rotational force. The increased pressure augments penetration of the pedicle screw through tissue without resort to sharp cutting edges.

20 Claims, 22 Drawing Sheets

Related U.S. Application Data a continuation-in-part of application No. PCT/US2018/030928, filed on May 3, 2018.

(60) Provisional application No. 62/867,616, filed on Jun. 27, 2019, provisional application No. 62/500,820, filed on May 3, 2017, provisional application No. 62/500,719, filed on May 3, 2017.

(58) Field of Classification Search
USPC ........ 606/264–278, 305, 306, 308, 311, 312, 606/314, 315, 318, 319, 323, 76
See application file for complete search history.

(56) References Cited

U.S. PATENT DOCUMENTS

| | | |
|---|---|---|
| 5,669,911 A | 9/1997 | Errico et al. |
| 5,672,176 A | 9/1997 | Biedermann et al. |
| 5,782,833 A | 7/1998 | Haider |
| 5,882,350 A | 3/1999 | Ralph et al. |
| 5,964,760 A | 10/1999 | Richelsoph |
| 6,022,352 A | 2/2000 | Vandewalle |
| 6,036,491 A | 3/2000 | Hansson |
| 6,074,391 A | 6/2000 | Metz-Stavenhagen |
| 6,149,432 A | 11/2000 | Shaw et al. |
| 6,248,105 B1 | 6/2001 | Schläpfer et al. |
| 6,296,642 B1 | 10/2001 | Morrison et al. |
| 6,306,140 B1 | 10/2001 | Siddiqui |
| 6,440,137 B1 | 8/2002 | Horvath et al. |
| 6,520,963 B1 | 2/2003 | McKinley |
| 6,585,737 B1 | 7/2003 | Baccelli et al. |
| 6,695,843 B2 | 2/2004 | Biedermann et al. |
| 6,835,196 B2 | 12/2004 | Biedermann et al. |
| 6,843,791 B2 | 1/2005 | Serhan |
| 7,018,378 B2 | 3/2006 | Biedermann et al. |
| 7,037,309 B2 | 5/2006 | Weil et al. |
| 7,156,850 B2 | 1/2007 | Kim |
| 7,211,086 B2 | 5/2007 | Biedermann et al. |
| 7,291,151 B2 | 11/2007 | Alvarez |
| 7,291,153 B2 | 11/2007 | Glascott |
| 7,445,627 B2 | 11/2008 | Hawkes et al. |
| 7,896,902 B2 | 3/2011 | Jeon et al. |
| 7,942,910 B2 | 5/2011 | Doubler et al. |
| RE42,545 E | 7/2011 | Ralph et al. |
| 8,034,085 B2 | 10/2011 | Slivka et al. |
| 8,080,036 B2 | 12/2011 | Shim et al. |
| 8,083,776 B2 | 12/2011 | Alvarez |
| 8,246,665 B2 | 8/2012 | Butler et al. |
| 8,257,402 B2 | 9/2012 | Jackson |
| 8,273,109 B2 | 9/2012 | Jackson |
| 8,337,532 B1 | 12/2012 | McLean et al. |
| 8,690,924 B2 | 4/2014 | Chin et al. |
| 8,702,758 B2 | 4/2014 | Wang et al. |
| 8,747,405 B2 | 6/2014 | Belliard |
| 8,808,292 B2 | 8/2014 | Velikov |
| 8,852,241 B2 | 10/2014 | Datta |
| 8,870,928 B2 | 10/2014 | Jackson |
| 9,011,505 B2 | 4/2015 | Prandi et al. |
| 9,023,087 B2 | 5/2015 | Frankel et al. |
| 9,079,263 B2 | 7/2015 | Reed |
| 9,161,788 B2 | 10/2015 | Daubs et al. |
| 9,277,950 B2 | 3/2016 | Buttermann |
| 9,339,310 B2 | 5/2016 | Dee et al. |
| 9,427,260 B2 | 8/2016 | Juchno et al. |
| 9,451,994 B1 | 9/2016 | Whipple et al. |
| 9,468,474 B2 | 10/2016 | Parikh et al. |
| 9,504,504 B2 | 11/2016 | Prandi et al. |
| 9,510,867 B2 | 12/2016 | Garamszegi |
| 9,782,204 B2 | 10/2017 | Spratt et al. |
| 9,782,209 B2 | 10/2017 | Reed |
| 9,943,340 B2 | 4/2018 | Whipple et al. |
| 10,064,707 B2 | 9/2018 | Zadeh |
| 10,149,702 B2 | 12/2018 | Ewer et al. |
| 10,238,432 B2 | 3/2019 | Carruth et al. |
| D847,994 S | 5/2019 | Asfora et al. |
| 10,653,455 B2 | 5/2020 | Lehman, Jr. et al. |
| 10,966,758 B2 | 4/2021 | Abbasi |
| 2002/0082602 A1 | 6/2002 | Biedermann et al. |
| 2003/0125741 A1 | 7/2003 | Biedermann et al. |
| 2003/0149436 A1 | 8/2003 | McDowell et al. |
| 2004/0006346 A1 | 1/2004 | Holmen et al. |
| 2004/0068261 A1 | 4/2004 | Fourcault et al. |
| 2004/0249380 A1 | 12/2004 | Glascott |
| 2005/0277928 A1 | 12/2005 | Boschert |
| 2006/0079895 A1 | 4/2006 | McLeer |
| 2007/0055238 A1 | 3/2007 | Biedermann et al. |
| 2008/0287998 A1 | 11/2008 | Doubler et al. |
| 2010/0094353 A1 | 4/2010 | Shim et al. |
| 2010/0125302 A1 | 5/2010 | Hammill, Sr. et al. |
| 2010/0160981 A1 | 6/2010 | Butler et al. |
| 2011/0190821 A1 | 8/2011 | Chin et al. |
| 2012/0130436 A1 | 5/2012 | Haskins et al. |
| 2012/0215263 A1 | 8/2012 | Lee |
| 2012/0271365 A1 | 10/2012 | Daugs et al. |
| 2013/0110183 A1* | 5/2013 | Duggal ................ A61B 17/809 606/328 |
| 2013/0238036 A1 | 9/2013 | Sinha |
| 2013/0345755 A1 | 12/2013 | Prajapati et al. |
| 2014/0094849 A1 | 4/2014 | Spratt et al. |
| 2014/0121703 A1 | 5/2014 | Jackson et al. |
| 2014/0135839 A1 | 5/2014 | Frankel et al. |
| 2014/0135854 A1 | 5/2014 | Dee et al. |
| 2014/0148858 A1 | 5/2014 | Dant et al. |
| 2014/0277188 A1* | 9/2014 | Poulos ............... B65D 43/0231 606/311 |
| 2014/0316475 A1 | 10/2014 | Parikh et al. |
| 2015/0196335 A1* | 7/2015 | Whipple ............ A61B 17/8635 606/312 |
| 2015/0351811 A1 | 12/2015 | Mclean et al. |
| 2016/0095638 A1 | 4/2016 | Reimels |
| 2016/0242817 A1 | 8/2016 | Abbasi |
| 2016/0278815 A1 | 9/2016 | Fitzpatrick |
| 2017/0303972 A1* | 10/2017 | Schumacher ........ A61B 17/863 |
| 2018/0014863 A1 | 1/2018 | Biester et al. |
| 2018/0228518 A1 | 8/2018 | Carruth et al. |
| 2018/0303529 A1* | 10/2018 | Zastrozna .......... A61B 17/8605 |
| 2020/0146725 A1* | 5/2020 | Geist .................. A61B 17/8625 |

FOREIGN PATENT DOCUMENTS

| | | |
|---|---|---|
| WO | WO2010037098 | 4/2010 |
| WO | WO2012140168 A1 | 10/2012 |
| WO | WO2014052117 | 4/2014 |
| WO | WO2014138736 | 9/2014 |

* cited by examiner

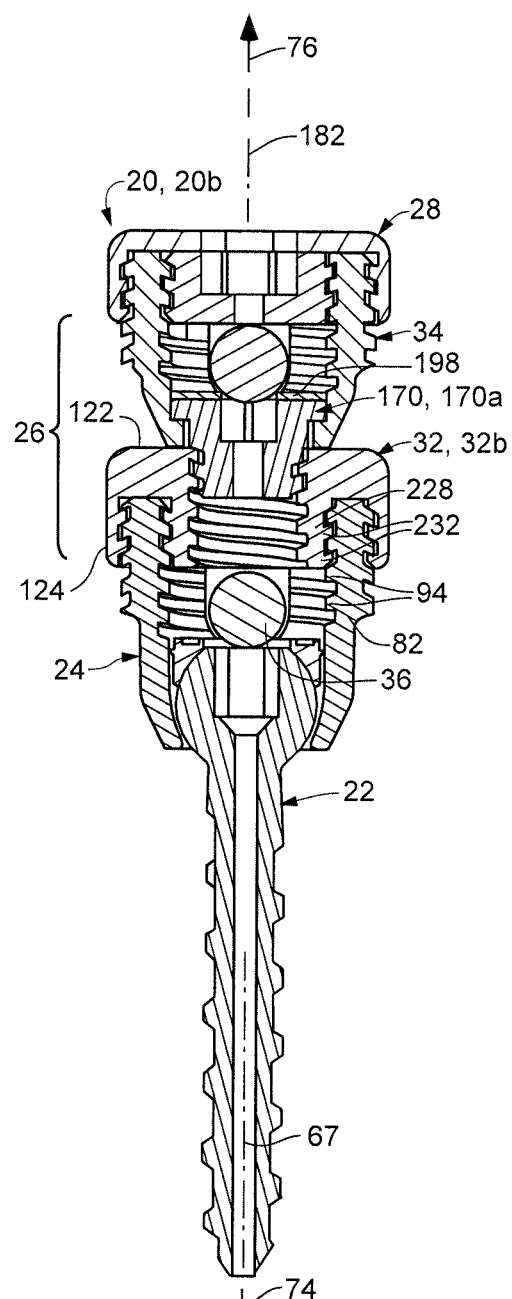
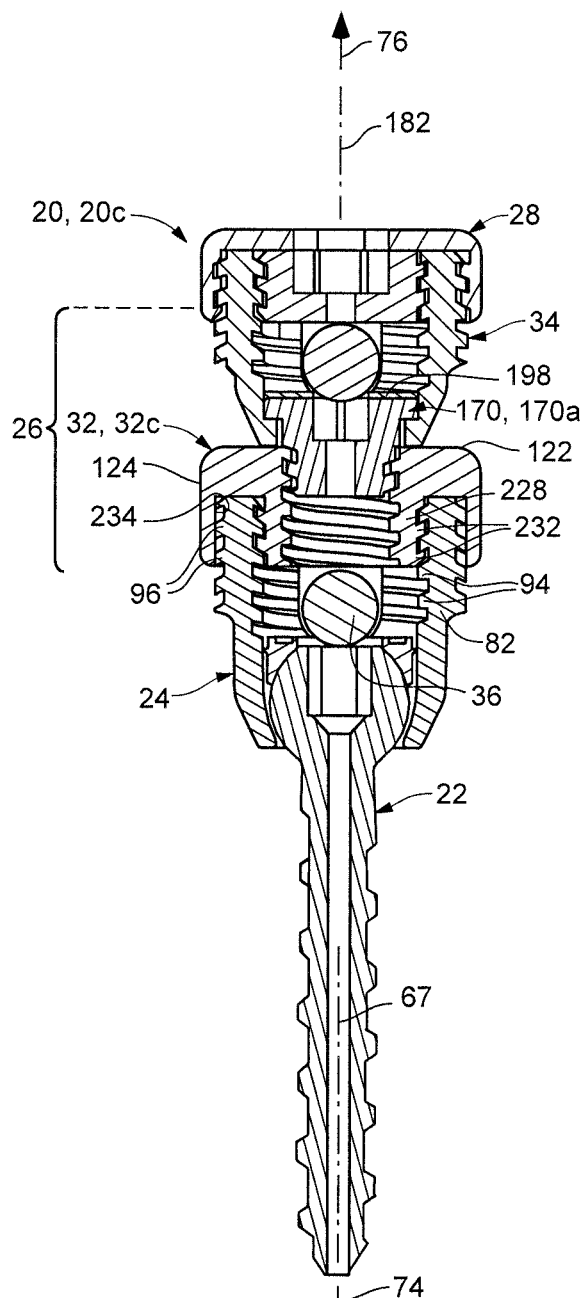
FIG. 6
FIG. 7

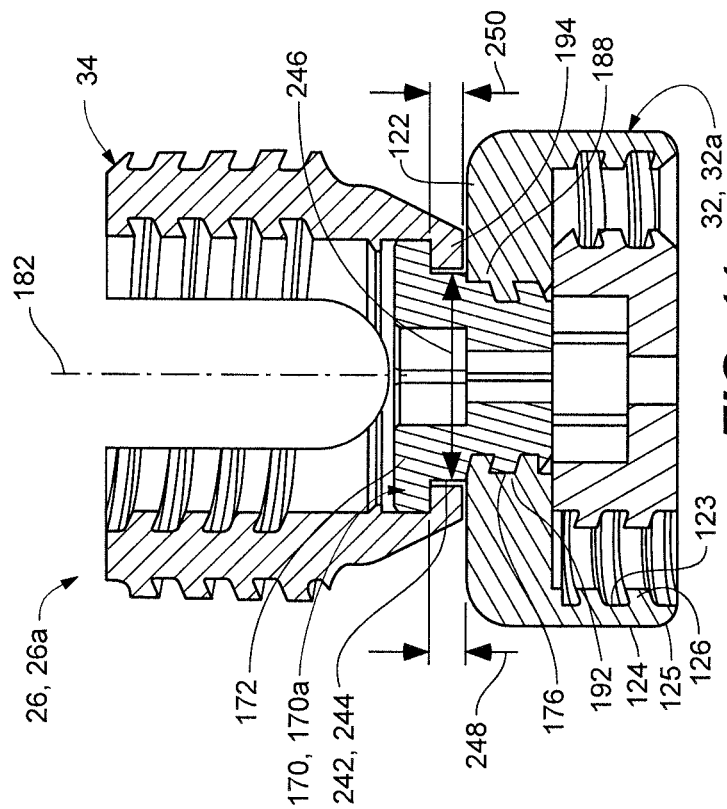
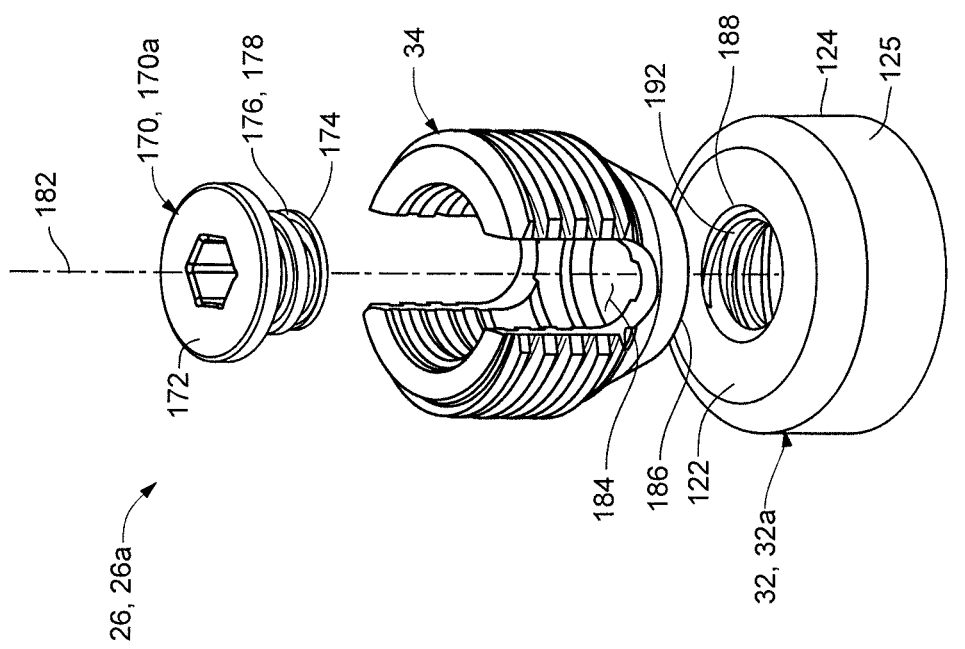

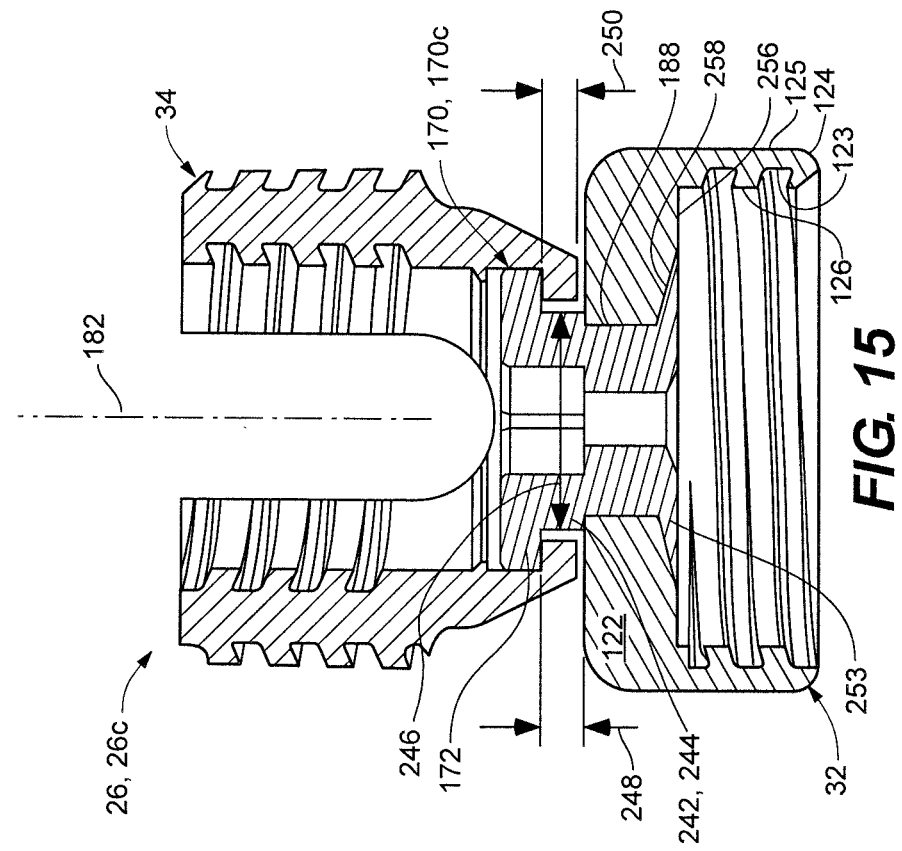
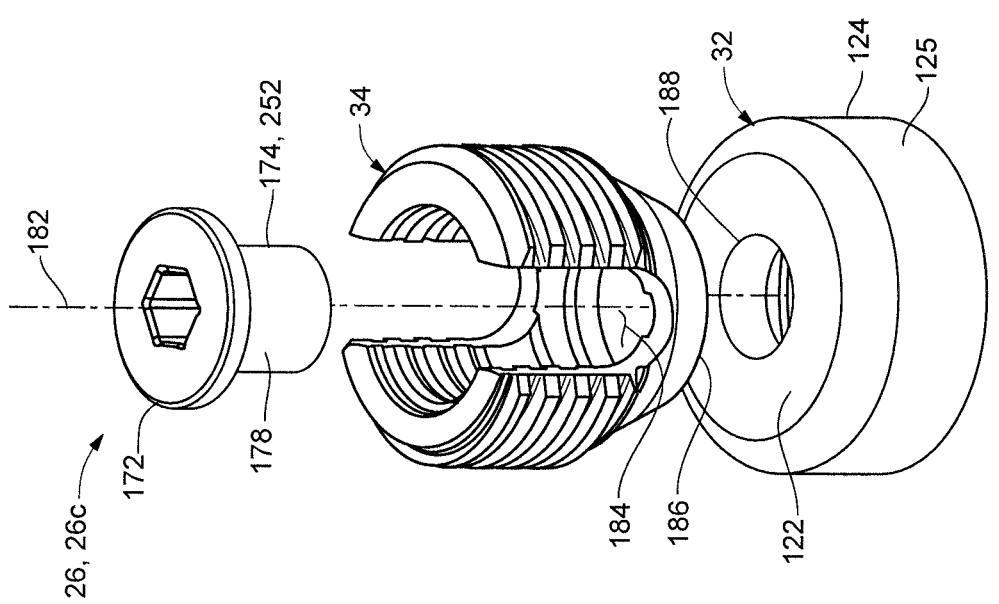

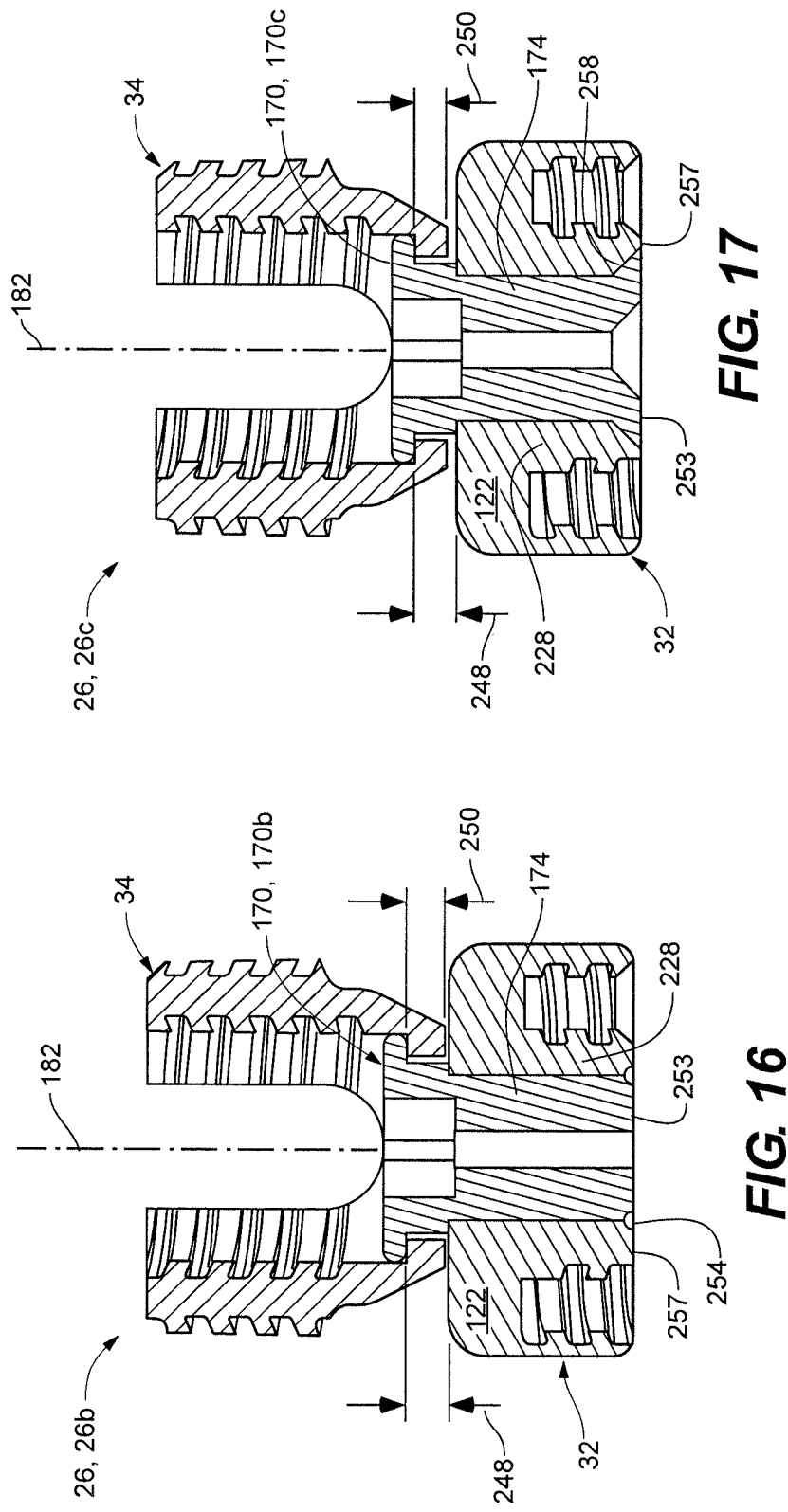

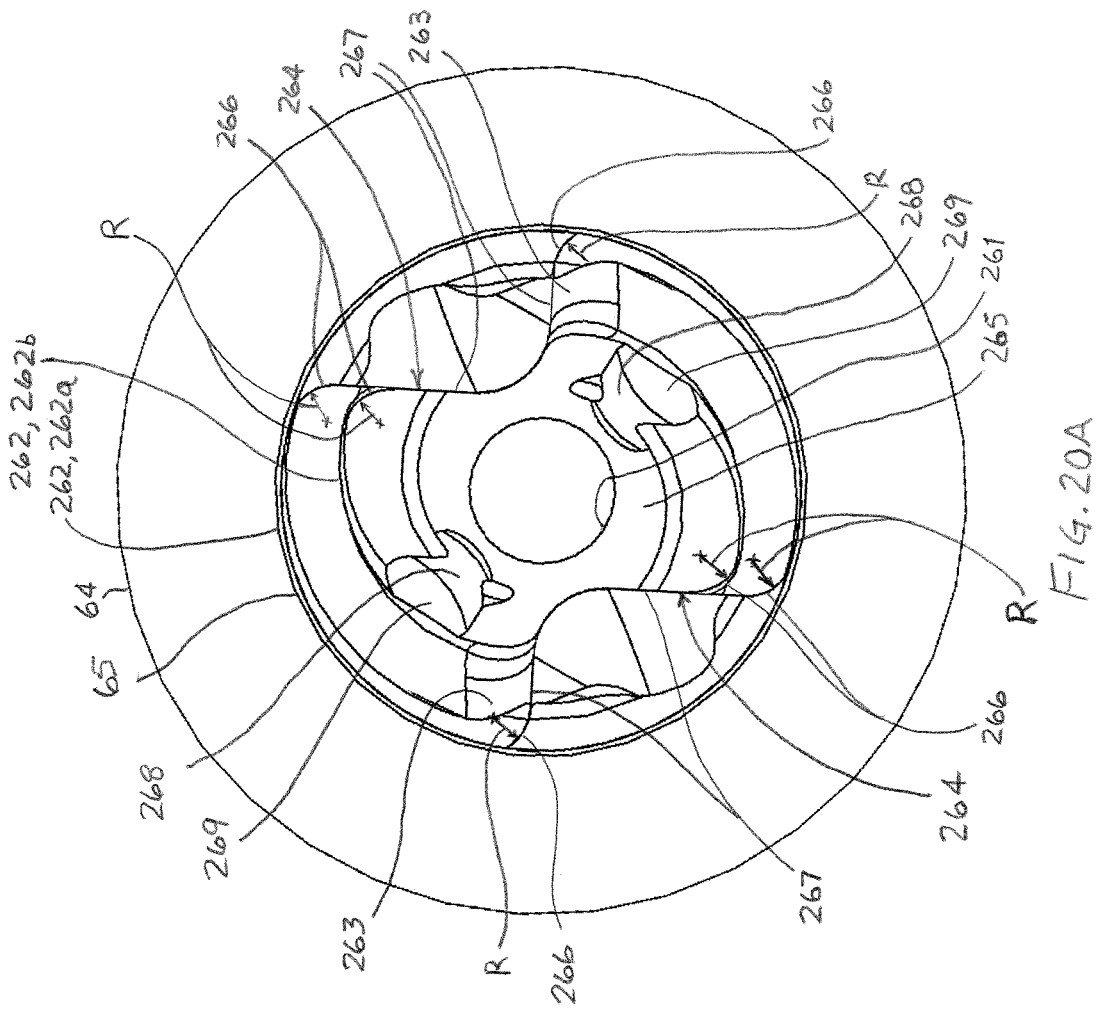
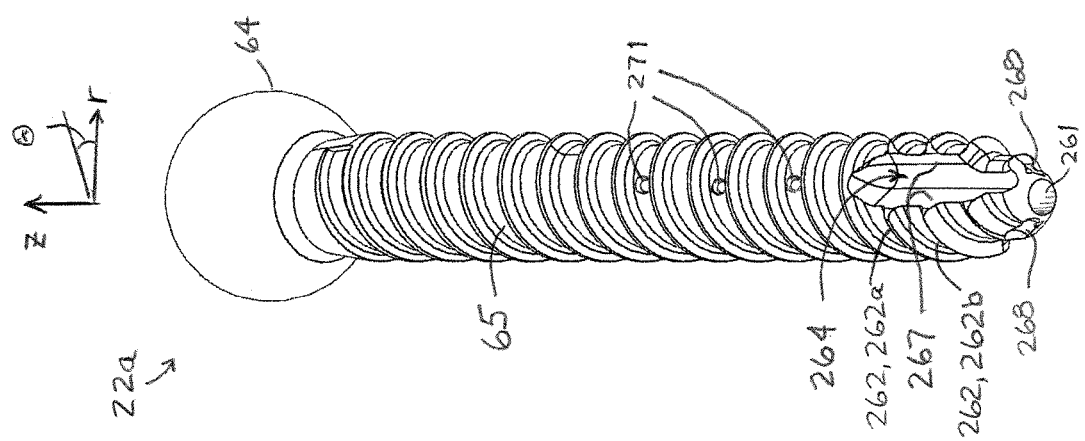

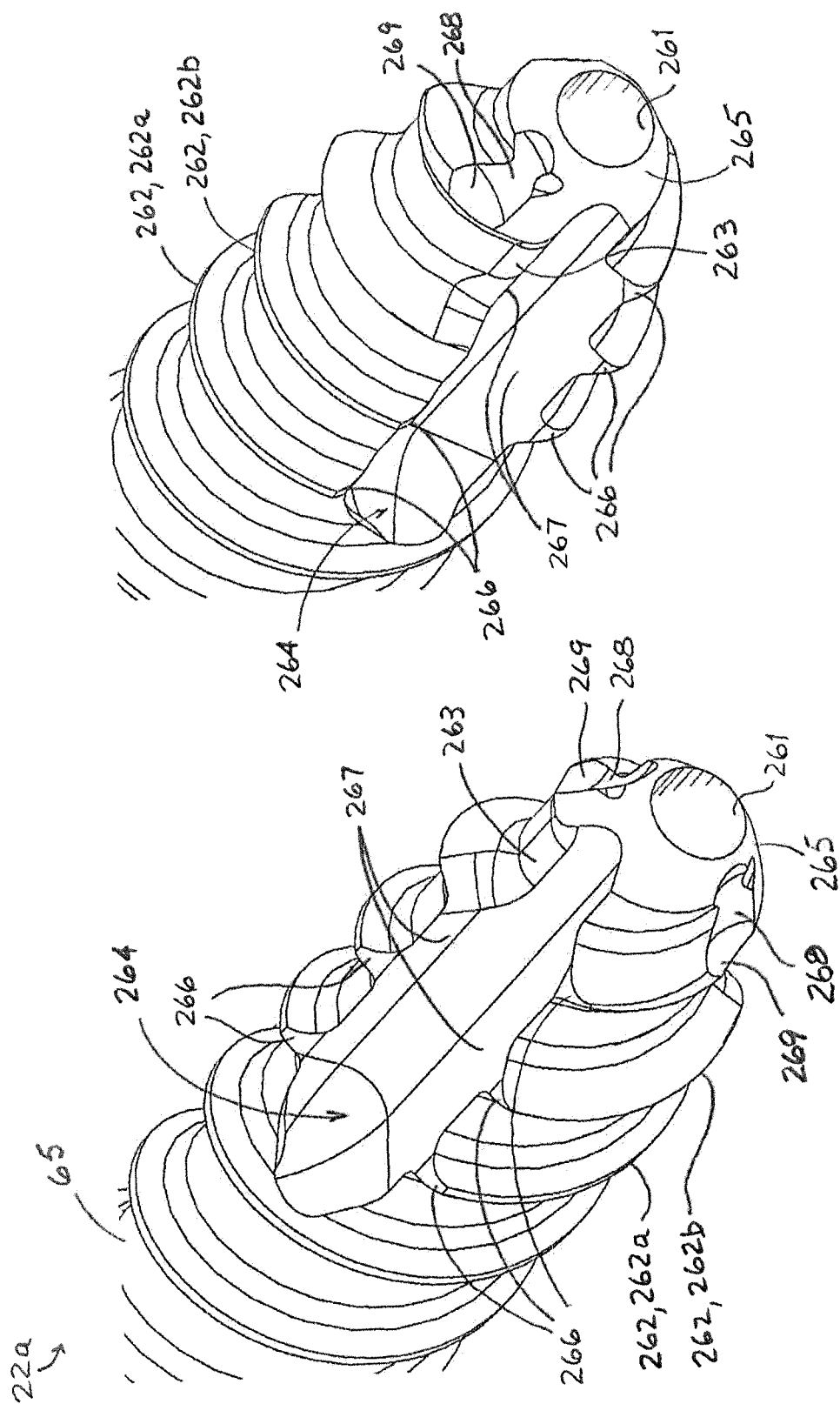

EXTENSION-READY SPINAL SUPPORT SYSTEM WITH VASCULAR-SAFE PEDICLE SCREW

RELATED APPLICATIONS

This application is a continuation-in-part of International Patent Application No. PCT/US2018/030928, filed May 3, 2018, and is a continuation-in-part of U.S. patent application Ser. No. 15/970,368, filed May 3, 2018, which claims the benefit of U.S. Provisional Patent Application No. 62/500,820, filed on May 3, 2017, and of U.S. Provisional Patent Application No. 62/500,719, filed May 3, 2017, the disclosures of which are hereby incorporated by reference herein in their entirety. This application also claims the benefit of U.S. Provisional Patent Application No. 62/867,616, filed Jun. 27, 2019, the disclosure of which is hereby incorporated by reference herein in its entirety.

FIELD OF THE DISCLOSURE

The present disclosure relates to spinal support systems and more particularly to spinal support systems that are readily extensive with pedicle screws that inhibit cutting or slicing of soft tissues.

BACKGROUND OF THE DISCLOSURE

Implementation of various spinal surgical techniques often requires the use of spinal support rods that are anchored to the vertebrae through the use of pedicle screws to provide stabilization of the spine during healing or correction. Examples include maintaining adjacent vertebrae stationary so that bone growth tissue can bridge the vertebrae in a spinal fusion process. Another example is the use of spinal support rods to apply a coercive force to the spine for corrective purposes (e.g., correction of scoliosis).

The pedicle screws are tapped into the vertebrae of the spine for the anchoring. The anatomy of the human body is such that the spine includes and is proximate to numerous vascular vessels. A concern is that the pedicle screw could contact and damage the vascular vessels during the tapping process.

Also, the spinal rods are typically disposed in rod receptacles at the head of the pedicle screw. The rod receptacles typically define diametrically opposed slots, with the spinal rod extending through the slots. The formation of the slots further define opposed wall segments that extend proximally on lateral sides of the spinal rod. The spinal rod is typically held within the slots with a set screw that threadably engages the wall segments. Over time, creep stresses may cause the wall segments to plastically deform radially outward and away from the set screw, with an accompanying decrease the clamping force of the set screw against the spinal rod due to loss of elasticity of the wall segments. This can cause loosening of the assembly and slippage of the resident spinal rod within the spinal rod receptacle. In some instances, torque requirements, particularly where the spinal rods are subject to high tension forces, can cause the set screw to slip within the spinal rod receptacle during implantation.

In some cases, surgery is later required to treat other vertebrae of the same patient. "Extension" systems have been developed which enable additional spinal support rods to be coupled to existing spinal rods or pedicle screws of the previous surgery, thereby reducing surgical trauma and recovery times. Such an extension system is found, for example, at U.S. Pat. No. 9,655,654 to Abbasi entitled "Spinal Rod Support Structure with Clamp," owned by the owner of the current application, the disclosure of which is incorporated by reference herein in its entirety except for patent claims and express definitions contained therein.

The present application identifies shortcomings and limitations in the art of spinal rod extension systems and provides improvements to remedy such shortcomings and limitations.

SUMMARY OF THE DISCLOSURE

Various embodiments of the disclosure are directed to a "vascular-safe" pedicle screw. The vascular-safe pedicle screw includes one or more self-tapping flutes that interrupt or terminate the threads at several points along the threads. These terminations are configured to push soft tissue aside as opposed to slicing or tearing through the soft tissue, so that the self-tapping flute is less likely to slice into vascular vessels, while still effectively tapping into bone tissue. The distal portion of the pedicle screw may also include features that reduce the circumferential contact area of the pedicle screw in the direction of rotation, to increase the applied pressure to the soft tissue for a given applied rotational force for augmenting penetration of the pedicle screw without resort to sharp cutting edges. Some embodiments of the disclosed pedicle screw are not only vascular-safe, but also self-tapping, self-steering, self-centering, or a combination thereof.

Various embodiments of the disclosure also provide an "extension ready" spinal support system that enables the extension to be accomplished with reduced disturbance to an existing spinal support structure relative to conventional extension systems. In some embodiments, existing connections between the existing spinal support rod and pedicle screws can remain intact while extension rod receptacles are mounted directly to the existing base rod receptacles. In some embodiments, the extension receptacle may be polyaxial with respect to the base receptacle. In some embodiments, the extension receptacle is provided with a low profile (i.e., shortened axial projection length from the base rod receptacle) relative to the polyaxial embodiment by eliminating polyaxial structure between the base receptacle and the extension receptacle and the additional axial lengths associated therewith and providing a monoaxial structure that rotates about but does not pitch relative to the extension axis.

In various embodiments of the disclosure, a spinal support system is disclosed where a unitary reinforcement cap threadably engages both the internal and the external surfaces of the wall segments of the rod receptacle. By doubling the number of threads that are engaged, additional strength and structural integrity are realized over standard set screw arrangements. Also, because of the unitary construction, wherein an internal set screw portion and an external skirt portion are integral to the reinforcement cap, lateral movement between the set screw portion and the skirt portion is limited.

In some embodiments, the unitary reinforcement cap does not threadably engage the external surface, but instead slides over the external surface to capture and support to the rod receptacle. Accordingly, such embodiments do not require threads on the external surface of the rod receptacle, and can be configured for a retrofit of conventional rod receptacles.

In some embodiments, the threads are of a canted cantilever construction, wherein the interfaces of threadably engaged components are tailored to generate reaction force vectors that prevent slippage at the interfaces.

Conventional spinal rod extension systems exist where extension spinal support rod receptacles (also referred to as extension "tulips" in the parlance of the spinal support arts) can be mounted "piggyback" to an existing or "base" spinal support rod receptacle. However, conventional systems require that the connection between the base spinal support rod receptacle be disturbed or modified. For example, in some systems, the set screw securing the base spinal rod to the base receptacle must be removed so that the extension receptacle can utilize the interior threads of the base receptacle. This releases the base spinal support rod from the base receptacle, thus requiring that the base spinal support rod be reset before the surgeon can proceed with implantation of the extension system. Often, the required structure that extends from the base receptacle is of undesirable axial length, causing concealment issues.

Another drawback of conventional rod receptacle arrangements is the separation or "splaying" of the tulip. When a conventional set screw is seated within a conventional tulip, forces are generated on the tulip wall portions that force the tulip wall sections away from each other. This separation of the tulip walls is referred to as "splaying."

Various embodiments of the disclosure alleviate one or more of these shortcomings and limitations. The disclosed embodiments enable extension of the spinal support structure without need for removing the tulips or pedicle screws of the already-implanted spinal support structure. Certain embodiments alleviate the need to remove the set screw from the interior threads of the base receptacle. As with conventional rod receptacles, the disclosed base rod receptacle includes interior threads to which a set screw is coupled for securing the base spinal support rod. In addition, the disclosed system further includes exterior threads to which an optional extension assembly can be mounted at a later time. By utilizing the exterior threads for mounting the extension system, the set screw that secures the base spinal support rod to the base rod receptacle does not have to be removed from the interior threads of the base rod receptacle. In this way, the base spinal support system can remain intact and undisturbed as the extension system is coupled thereto.

Other embodiments may involve removal of the set screw from the base receptacle, but utilize a reinforced, dual threaded or capped base that is stronger and more robust than standard set screw arrangements and prevents splaying of the tulip.

Structurally, the vascular-safe pedicle screw comprises a head portion, a threaded shaft portion distal to the head portion and including threads that extend to a distal end portion of the threaded shaft portion, and a self-tapping flute at the distal end portion of the threaded shaft portion. The self-tapping flute is recessed into the threaded shaft to define at least one terminated thread at a face of the self-tapping flute. In some embodiments, the terminated threads are curved to define a convex profile that extends in a tangential direction from proximate a root of the at least one terminated thread at the face of the self-tapping flute to a crest of the at least one terminated thread. The distal end portion of the threaded shaft portion may also define a depression at a leading end of the thread. In some embodiments, the head portion and the threaded shaft portion define a central passage that passes therethrough. The threaded portion may define a plurality of fenestrations that are in fluid communication with the central passage. In some embodiments, the threads are double threads. The threaded shaft portion may include dulled edges, for example polished or roughened edges. In some embodiments, the threaded shaft portion defines a surface roughness having arithmetical mean deviation that is in a range of 5 micrometers to 15 micrometers inclusive.

In various embodiments of the disclosure, a spinal rod support system is disclosed, comprising a pedicle screw, including a head portion, a threaded shaft portion distal to the head portion and including threads that extend to a distal end portion of the threaded shaft portion, and a self-tapping flute at the distal end portion of the threaded shaft portion, the self-tapping flute being recessed into the threaded shaft to define terminations of the threads at a face of the self-tapping flute, the terminations being defining a convex profile that extends in a tangential direction from a root to a crest of the threads at the face of the self-tapping flute. In some embodiments, the spinal rod support system includes a base rod receptacle coupled to the pedicle screw, and an extension rod receptacle configured to couple to the base rod receptacle. The threaded shaft portion may include dulled edges. In some embodiments, a base portion is configured to threadably couple to the base rod receptacle, the base portion including a skirt portion that extends from a mounting platform, the mounting platform defining a center hole accessible from a proximal face of the mounting platform, the extension rod receptacle extending into the center hole. The base rod receptacle may define exterior threads, with the skirt portion of the base defining interior threads configured to mate with the exterior threads of the base rod receptacle. In some embodiments, the spinal rod support system comprises a reinforcement cap configured to couple to one of the base rod receptacle and the extension rod receptacle, the reinforcement cap including a set screw portion and a skirt portion, wherein the base rod receptacle defines interior threads, the extension rod receptacle defines interior threads, and the set screw portion of the reinforcement cap defines exterior threads configured to mate with either of the interior threads of the base rod receptacle or the interior threads of the extension rod receptacle. In some embodiments, the extension rod receptacle defines exterior threads. The skirt portion of the reinforcement cap may define interior threads configured to mate with either of the exterior threads of the base rod receptacle or the exterior threads of the extension rod receptacle.

In some embodiments, a "reverse canted cantilever" arrangement is disclosed, wherein the interior threads of the base rod receptacle and the interior threads of the extension rod receptacle each define a first canted cantilever profile that extends radially inward and in a distal direction, and the exterior threads of the base rod receptacle and the exterior threads of the extension rod receptacle each define a second canted cantilever profile that extends radially outward and in a proximal direction.

In various embodiments of the disclosure, a spinal support system comprises a first rod receptacle for mounting to a pedicle screw, the first rod receptacle having a first side wall that includes a first interior surface and a first exterior surface. The first side wall defines a first pair of diametrically opposed slots that extend axially along the first side wall and are open at a proximal end of the first rod receptacle, the first interior surface defining first interior threads. A first set screw includes threads configured to mate with the first interior threads of the first rod receptacle. The first exterior surface defines first exterior threads. An extension assembly including a base portion mounted to a second rod receptacle, the base portion including a mounting platform and a skirt portion that extends from the mounting platform, the skirt portion including interior threads for mating with the first exterior threads of the first rod receptacle, the second rod receptacle having a second side wall that includes a second interior surface and a second exterior surface. The second exterior surface of the second rod receptacle may include second exterior threads. The second side wall defines a second pair of diametrically opposed slots that extend axially along the second side wall and are open at a proximal end of the second rod receptacle, the second interior surface defining second interior threads. A second set screw includes threads configured to mate with the second interior threads of the second rod receptacle.

The extension assembly may include a pivot member that attaches the second rod receptacle to the base portion, the pivot member including a head portion and a shaft portion, the shaft portion including shaft threads formed on an exterior surface thereof, the shaft portion defining a pivot axis. In some embodiments, the second rod receptacle defines an opening at a distal end thereof, the opening sized to accommodate passage of the shaft portion of the pivot member. The mounting platform of the base portion may define a center hole for receiving the pivot member, and may include interior threads for mating with the external shaft threads. In some embodiments, the center hole is a through hole.

In some embodiments, the second rod receptacle includes an internal flange having an interior face, the head portion of the pivot member being dimensioned to register against the interior face of the internal flange to secure the second rod receptacle to the base portion. The head portion of the pivot member may be one of a flat head and a countersink head, and the interior face of the internal flange of the second rod receptacle may conforms to the head portion to enable selective monoaxial rotation about the pivot axis.

In some embodiments, a pedicle screw coupled to a distal end portion of the first rod receptacle. The pedicle screw and the first rod receptacle may be configured for polyaxial rotation of the first rod receptacle about a head of the pedicle screw. In some embodiments, a lock ring configured to engage a spinal support rod, the lock ring including a distal face that conforms to the pedicle screw and a proximal face that includes one or more malleable features for engaging the spinal support rod. The one or more malleable features may be plastically deformable. In some embodiments, the one or more malleable features includes a raised ridge. In some embodiments, the raised ridge is annular ring.

Some embodiments include a cap including a skirt portion having interior threads for mating with the second exterior threads of the second rod receptacle. In some embodiments, the skirt portion is not threaded, but instead slides over the exterior of the base rod receptacle to prevent splaying. An exterior surface of the skirt portion may define a plurality of flats, each of said plurality of flats being parallel to the pivot axis. In some embodiments, one or more of the first interior threads, the first exterior threads, the second interior threads, the second exterior threads, and the internal threads of the center hole define a canted cantilever profile. The canted cantilever profile may extend radially and variously in a distal direction or a proximal direction.

In various embodiments of the disclosure, a spinal rod support system comprises an extension rod receptacle, a base portion including a mounting platform that defines a center hole accessible from a proximal face of the mounting platform, and means for coupling the extension rod receptacle to the base portion. In some embodiments, the means for coupling the extension rod receptacle to the base portion includes a pivot member threadably engaged with the center hole. In some embodiments, the means for coupling the extension rod receptacle to the base portion includes a pivot member swaged to the center hole. In some embodiments, the means for coupling the extension rod receptacle to the base portion includes a pivot member fused to the center hole. The pivot member may be welded to the center hole at a distal face of the base portion, for example, a distal face of the mounting platform.

The spinal support system may further comprise a base rod receptacle, and means for coupling the base portion to the base rod receptacle. In some embodiments, the base portion includes a skirt portion, and the means for coupling the base portion to the base rod receptacle includes threaded engagement of the skirt portion to the base rod receptacle. In some embodiments, the base portion includes a set screw portion that is unitary with and extends from a distal face of the mounting platform, and the means for coupling the base portion to the base rod receptacle includes threaded engagement of the set screw portion to the base rod receptacle. In some embodiments, the set screw portion and the base portion include mating threads that define canted cantilever profiles for the threaded engagement. The canted cantilever profiles may extend radially and in a distal direction. In some embodiments, the spinal support system comprises a base spinal support rod disposed in the base rod receptacle, the set screw portion being configured to clamp the base spinal support rod within the base rod receptacle. In some embodiments, the base portion includes a set screw portion that is unitary with and extends from a distal face of the mounting platform, and the means for coupling the base portion to the base rod receptacle includes threaded engagement of the set screw portion to the base rod receptacle. In some embodiments, the means for coupling the extension rod receptacle to the base portion enables only monoaxial rotation of the extension rod receptacle about a pivot axis.

In various embodiments of the disclosure, a method of fabricating an extension assembly for a spinal support system comprises: inserting a pivot member into a rod receptacle so that a shaft portion of the pivot member extends from a distal end of the rod receptacle; disposing the shaft portion in a center hole of a base portion so that an internal flange of the rod receptacle is captured between a head portion of the pivot member and the base portion so that an axial gap dimension defined between the head portion and the base member is greater than an axial thickness of the internal flange; and securing the pivot member to the base portion. In some embodiments, the step of disposing and the step of securing includes threadably engaging the shaft portion with the center hole. In some embodiments, the step of disposing includes registering a stop on the pivot member against the base portion to define the axial gap dimension. In some embodiments, the step of securing includes one of fusing and swaging the shaft member to the base portion.

In various embodiments of the disclosure, a reinforcement cap is disclosed for a spinal support system, comprising: a platform portion including a distal face and a proximal face separated by a perimeter portion; a skirt portion that extends from the distal face of the platform portion, the skirt portion including an interior surface, at least a portion of the interior surface including interior threads formed thereon; and a set screw portion that extends from the distal face of the platform portion, the set screw portion being surrounded by the skirt portion and including an exterior surface that faces radially outward, at least a portion of the exterior surface including exterior threads formed thereon, the set screw portion defining a rotation axis, the set screw portion and the skirt portion being concentric about the rotation axis to define an annular gap between the exterior threads of the set screw portion and the interior threads of the skirt portion. The skirt portion may include an exterior surface that is tangential with the perimeter portion. In some embodiments, the set screw portion extends distally beyond the skirt portion. The skirt portion may include an exterior surface that defines a plurality of flats, each of the plurality of flats being parallel to the rotation axis.

In some embodiments, the exterior threads of the set screw portion define a canted cantilever profile. Likewise, in some embodiments, the interior threads of the skirt portion define a canted cantilever profile. The canted cantilever profile of the set screw portion may slope in a distal direction and toward the rotation axis. The canted cantilever profile of the set screw portion may slope in a distal direction and away from the rotation axis.

In some embodiments, the platform portion defines a socket accessible from the proximal face, the socket being concentric with and extending along the rotation axis. The platform portion may also define a tapped center hole accessible from the proximal face, the tapped center hole being concentric with and extending along the rotation axis, the socket extending distally from the tapped center hole. The reinforcement cap may further define a center passage concentric with the rotation axis and extending from the socket through a distal end of the set screw portion.

In various embodiments of the disclosure, a spinal support system comprises the reinforcement cap as described above; and a spinal rod receptacle having a side wall that includes an interior surface and an exterior surface, the side wall defining a pair of diametrically opposed slots that extend axially along the side wall and are open at a proximal end of the spinal rod receptacle, the interior surface of the spinal rod receptacle defining interior threads, the exterior surface of the spinal rod receptacle defining first exterior threads, wherein the interior threads of the spinal rod receptacle are configured to mate with the exterior threads of the set screw portion of the reinforcement cap, and the exterior threads of the spinal rod receptacle are configured to mate with the interior threads of the skirt portion of the reinforcement cap. In various embodiments, a spinal rod is configured for insertion into the diametrically opposed slots. A pedicle screw may be disposed within the spinal rod receptacle, a shaft of the pedicle screw extending distally from the spinal rod receptacle.

In various embodiments of the disclosure, a method for securing a spinal support rod to a spinal rod receptacle is disclosed, comprising: (a) disposing a spinal support rod through diametrically opposed slots of a spinal rod receptacle; (b) threadably engaging interior threads of a skirt portion of a reinforcement cap with exterior threads of the spinal rod receptacle; (c) simultaneously with step (b), threadably engaging exterior threads of a set screw portion of the reinforcement cap with interior threads of the spinal rod receptacle; and (d) tightening the reinforcement cap against the spinal support rod. In some embodiments, step (d) includes driving the reinforcement cap with a tool that mates with a socket formed on the reinforcement cap. In some embodiments, step (d) includes driving the reinforcement cap with a tool that engages flats formed on the skirt portion of the reinforcement cap.

BRIEF DESCRIPTION OF THE DRAWINGS

FIGS. 6 through 8 are sectional views of alternative extensible spinal support systems in full assembly with the extension ready base assembly of FIG. 1 according embodiments of the disclosure;

FIGS. 10 and 11 are sectional views depicting assembly of an extension sub-assembly having a threaded pivot member according to an embodiment of the disclosure;

FIGS. 14 and 15 are sectional views depicting assembly of an extension sub-assembly having a riveted pivot member according to an embodiment of the disclosure;

FIGS. 16 and 17 are sectional views of extension sub-assemblies with base portions that have integral set screw portions according to an embodiment of the disclosure;

FIG. 19 is a perspective view of an alternative pedicle screw according to an embodiment of the disclosure;

FIG. 20A is an enlarged, distal end view of the pedicle screw of FIG. 19 according to an embodiment of the disclosure;

FIGS. 20B and 20C are an enlarged, partial perspective views of the pedicle screw of FIG. 19 according to an embodiment of the disclosure;

DETAILED DESCRIPTION OF THE FIGURES

Figure 1:
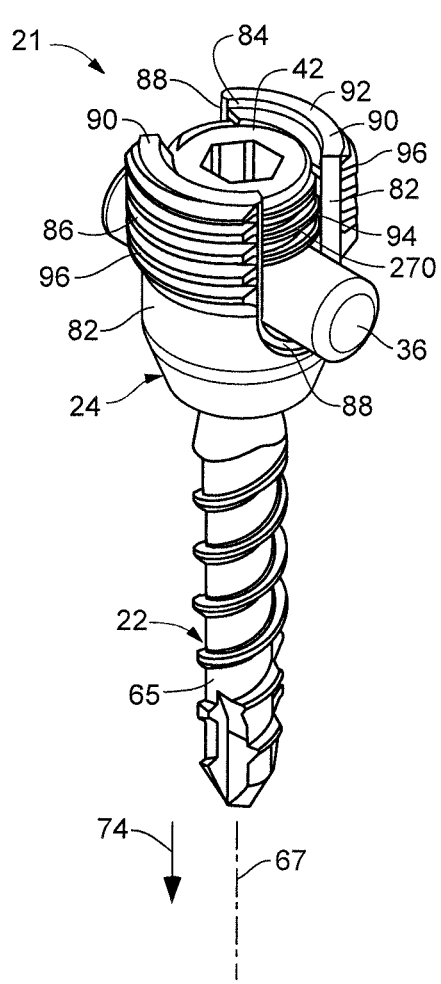
FIG. 1 is a perspective view of an extension ready base assembly according to an embodiment of the disclosure.
Figure 2:
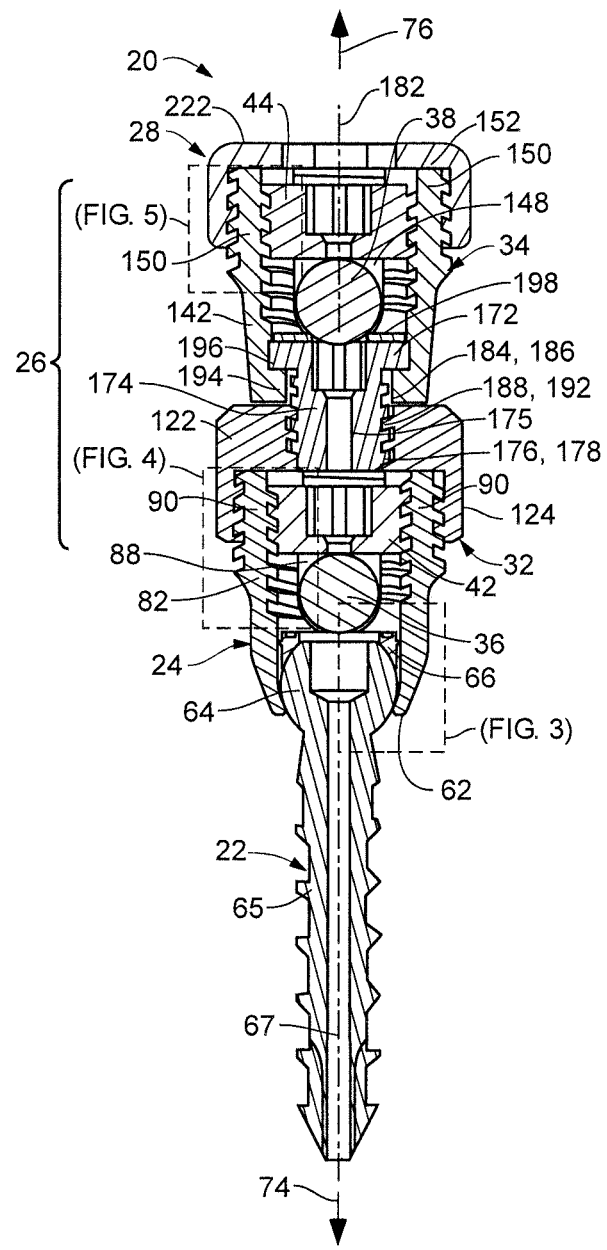
FIG. 2 is a sectional view of an extensible spinal support system in full assembly with the extension ready base assembly of FIG. 1 according an embodiment of the disclosure.

Referring to FIGS. 1 through 5, an extensible spinal support system 20 is depicted according to an embodiment of the disclosure. The extensible spinal support system 20 as depicted includes an extension ready base assembly 21 including a pedicle screw 22, a first or base rod receptacle 24, a first or base set screw 42, and a first spinal support rod 36 (FIG. 1). The extensible spinal support system 20 further includes an extension subassembly 26 and a cap 28 (FIG. 2). The extension subassembly 26 includes a base portion 32 and a second or extension rod receptacle 34. The base rod receptacle 24 is configured to receive the first or base spinal support rod 36, and the extension rod receptacle 34 is configured to receive a second or extension spinal support rod 38. In the depicted embodiments, the base spinal support rod 36 is retained within the base rod receptacle 24 with the base set screw 42. Likewise, for the extensible spinal support system 20, the extension spinal support rod 38 is retained within the extension rod receptacle 34 with a second or extension set screw 44.

The pedicle screw 22 includes a head portion 64 and a threaded shaft portion 65 centered about a central axis 67. The pedicle screw 22 extends from a distal end 62 of the base rod receptacle 24, the head portion 64 being captured within the distal end 62 of the base rod receptacle 24. In some embodiments, a lock ring 66 is captured between the base spinal support rod 36 and the head portion 64 of the pedicle screw 22. In the depicted embodiment, the head portion 64 of the pedicle screw 22 defines a spherical surface portion 68, with the base rod receptacle 24 including a complementary mating surface 72 that engages and conforms to the spherical surface portion 68 of the head portion 64 of the pedicle screw 22.

Functionally, the spherical surface portion 68 of the head portion 64 of the pedicle screw 22 and the complementary mating surface 72 of the base rod receptacle 24 enable the base rod receptacle 24 to pitch about the head portion 64 of the pedicle screw 22 relative to the central axis 67, and to rotate about the head portion 64 in the pitched orientations. By this arrangement, the pedicle screw 22 and the base rod receptacle 24 are configured for polyaxial rotation of the base rod receptacle 24 about the head portion 64 of the pedicle screw 22.

Herein, "proximal" refers to a direction 76 that is toward a surgeon during operation or implantation and away from a bone or patient. "Distal" refers to a direction 74 that is away from the surgeon during operation or implantation and toward the bone or patient to which the extensible spinal support system 20 is implanted (i.e., a direction opposite the proximal direction 76).

Figure 1A:
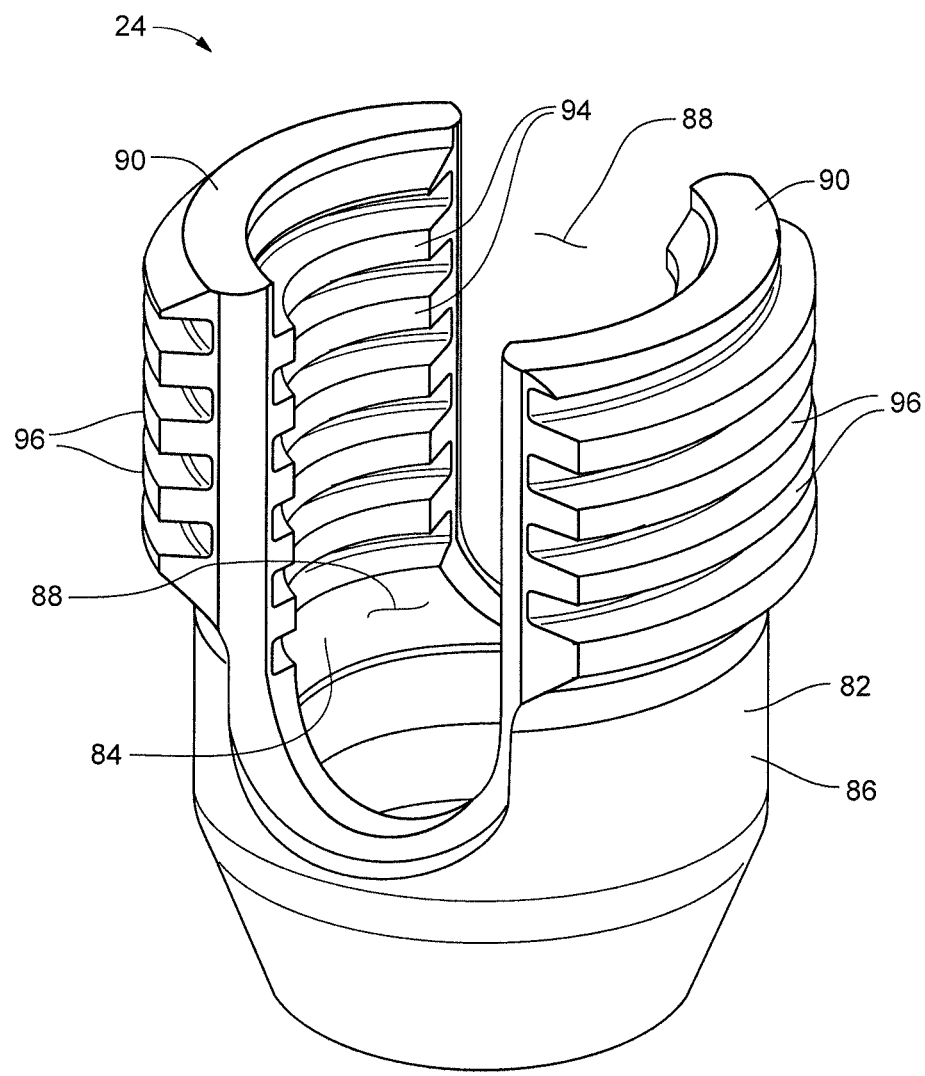
FIG. 1A is an upper perspective view of a base rod receptacle of FIG. 1 in isolation according to an embodiment of the disclosure.

The base rod receptacle 24 includes a side wall 82 having an interior surface 84 and an exterior surface 86 (FIG. 1A). A pair of diametrically oppose slots 88 are defined on the side wall 82, the slots 88 extending axially along the side wall 82 and being open at a proximal end 92 of the base rod receptacle 24. By formation of the diametrically opposed slots 88, the side wall 82 defines diametrically opposed wall segments 90 on opposing sides of the diametrically opposed slots 88. The interior surface 84 extends axially along the side wall 82 and includes interior threads 94 formed thereon. The exterior surface 86 also extends axially and includes exterior threads 96 formed thereon. The base portion 32 of the extension subassembly 26 includes a mounting platform 122 and a skirt portion 124 that extends from the mounting platform 122 in the distal direction 74. The skirt portion 124 includes an interior surface 123 and an exterior surface 125.

Figure 5:
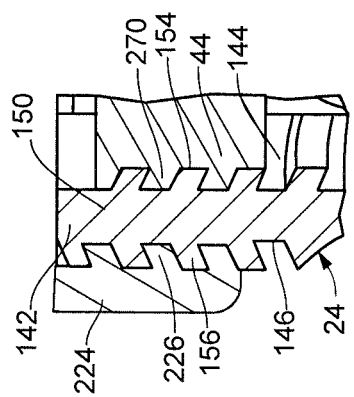
FIG. 5 is an enlarged, partial sectional view of a threaded wall portion of an extension rod receptacle of the assembly of FIG. 2 according to an embodiment of the disclosure.
Figure 4:
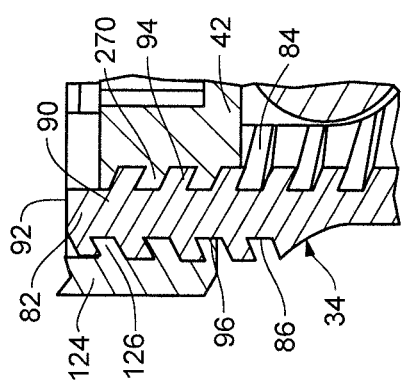
FIG. 4 is an enlarged, partial sectional view of a threaded wall portion of a base rod receptacle of the assembly of FIG. 2 according to an embodiment of the disclosure.
Figure 3:
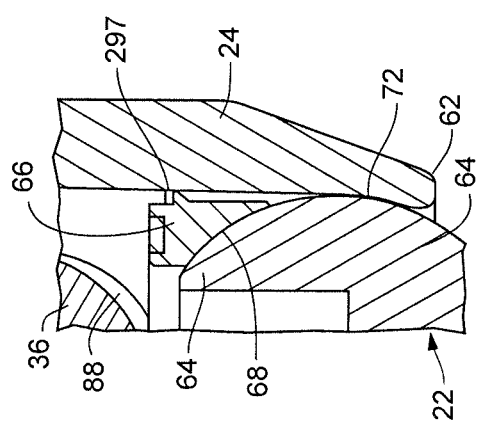
FIG. 3 is an enlarged, partial sectional view of a lock ring in the assembly of FIG. 2 according to an embodiment of the disclosure.

The extension rod receptacle 34 includes a side wall 142 having an interior surface 144 and an exterior surface 146. A pair of diametrically opposed slots 148 are defined on the side wall 142, the slots 148 extending axially along the side wall 142 and being open at a proximal end 152 of the extension rod receptacle 34. By formation of the diametrically opposed slots 148, the side wall 142 defines diametrically opposed wall segments 150 on opposing sides of the diametrically opposed slots 148. The interior surface 144 extends axially along the side wall 142 and includes interior threads 154 formed thereon (FIG. 5). The exterior surface 146 also extends axially and includes exterior threads 156 formed thereon.

In the depicted embodiment, the extension subassembly 26 includes a pivot member 170 that attaches the extension rod receptacle 34 to the base portion 32, the pivot member 170 including a head portion 172 and a shaft portion 174 and defining a through passage 175. In assembly, the shaft portion 174 is concentric with a pivot axis 182 about which the extension rod receptacle 34 is rotatable. The extension rod receptacle 34 defines an opening 184 at a distal end 186 thereof. The opening 184 is sized to accommodate passage of the shaft portion 174 of the pivot member 170.

In the depicted embodiment, the mounting platform 122 of the base portion 32 defines a center hole 188 for receiving the pivot member 170. The extension rod receptacle 34 may include an internal flange 194 having an interior face 196, the head portion 172 of the pivot member 170 being dimensioned to extend radially over the interior face 196 of the internal flange 194 to loosely secure the extension rod receptacle 34 to the base portion 32. The head portion 172 of the pivot member 170 may be one of several head styles available to the artisan, for example a flat head (depicted), a socket head, a countersink head, or a spherical head. The interior face 196 of the internal flange 194 may be configured to conform to the head portion 172. In some embodiments, a collet 198 is disposed interstitially between the extension spinal support rod 38 and the head portion 172. The collet 198 may be a disc spring (depicted), lock washer, or other that exerts a bias force parallel to the pivot axis 182 when compressed between the support rod 38 and the head portion 172. The cap 28 includes a top portion 222 and a skirt portion 224 that extends from the mounting platform 222. The skirt portion 224 includes interior threads 226 for mating with the exterior threads 156 of the extension rod receptacle 34.

In operation, the pedicle screw 22 is inserted into the base rod receptacle 24 so that the head portion 64 of the pedicle screw 22 can be registered against the mating surface 72 of the base rod receptacle 24. The pedicle screw 22 is set into the bone of a vertebrae. The lock ring 66, if utilized, is disposed within the base rod receptacle 24 and arranged for contact with the head portion 64 of the pedicle screw 22. The base rod receptacle 24 is arranged in a desired orientation on the head portion 64 of the pedicle screw 22 and the base spinal support rod 36 disposed in the base rod receptacle 24. The lock ring 66 is thereby disposed between the base spinal support rod 36 and the head portion 64 of the pedicle screw 22. The base set screw 42 is threadably engaged with the interior threads 94 of the side wall 82 and tightened so that the base spinal support rod 36 is clamped between the base set screw 42 and the lock ring 66 (if utilized) or, alternatively, the head portion 64 of the pedicle screw 22. The tightening of the base set screw 42 also seats the head portion 64 of the pedicle screw 22 against the mating surface 72 of the base rod receptacle 24 to secure the base rod receptacle 24 in the desired orientation relative to the head portion 64.

Referring to FIGS. 6 and 7 and again to FIG. 2, extensible spinal support systems 20 having alternative embodiments for the base portion 32 are presented according to embodiments of the disclosure. In FIGS. 2, 6, and 7, the extensible spinal support systems and their associated base portions are referred to collectively and generically by reference characters 20 and 32, respectively, and specifically by the reference characters 20 and 32 followed by a letter suffix (e.g., extensible spinal support system 20*a* and the associated base portion 32*a*). Several components and attributes are common to all extensible spinal support systems 20, which are indicated with same numbered reference characters.

For the extensible spinal support system 20*a* (FIG. 2), the base portion 32*a* and the base set screw 42 are separate components that are installed independently of each other. For the extensible spinal support systems 20*a* and 20*b*, the skirt portion 124 includes interior threads 126 for mating with the exterior threads 96 of the base rod receptacle 24. For the extensible support system 20*b* (FIG. 6), the base portion 32*b* additionally includes a set screw portion 228 that is integral therewith, the set screw portion 228 having external threads 232 that mate with the interior threads 94 of the side wall 82 of the base rod receptacle 24. Accordingly, for the extensible spinal support system 20*b*, the external threads 232 of the set screw portion 228 and the interior threads 226 of the skirt portion 124 of the base portion 32*b* are threaded simultaneously. For the extensible spinal support system 20*c* (FIG. 7), the base portion 32*c* also includes the set screw portion 228 that is integral therewith, and having external threads 232 that mate with the interior threads 94 of the side wall 82 of the base rod receptacle 24. However, for the extensible spinal support system 20*c*, an inner surface 234 of the skirt portion 124 is smooth (does not include interior threads), such that the skirt portion 124 rotates about and slides over but does not threadably engage the exterior threads 96 of the base rod receptacle 24. Accordingly, the base portion 32*c* mates only with the interior threads 94 of the side wall 82.

By integrating the set screw portion 228 with the mounting platform 122 as in subassemblies 26*b* and 26*c*, and skirt portion 124 the structural integrity of the extensible spinal support system 20 is enhanced. For example, lateral forces applied to the extensible spinal support system 20 will incur greater resistance because the set screw portion 228 is integrated with (e.g., unitary with) the mounting platform 122, establishing a shear stress at the junction of the integrated set screw portion 228 and the mounting platform 122 that provides additional resistance to deformation relative to the extension subassemblies 26 of FIGS. 10 through 15.

Functionally, each of the extensible support systems 20 provide a unique advantage. Extensible spinal support system 20*a* enables mounting of the extension assembly 26 without disturbing the base set screw 42, eliminating the need to reset the base spinal support rod 36. The extensible spinal support system 20*a* may find application where disturbance of the base spinal support system is not necessary or is ill advised. The extensible spinal support system 20*b* provides a dual threaded arrangement that enhances structural integrity of the extension assembly 26 to the base rod receptacle 24. Such enhancement of the structural integrity may be advantageous for high torque and high stress applications, such as scoliosis correction. Extensible spinal support system 20*c* also includes the integrated set screw portion 228 and attendant benefit while the smooth, sliding fit of the skirt portion 124 enables easier installation where the dual threaded arrangement of the extensible spinal support system 20*b* may be unnecessary or difficult. The sliding fit of the skirt portion 124 for the extensible spinal support system 20*c* effectively captures the side walls 82 of the base rod receptacle 24 to limit splaying. The extensible spinal support system 20*c* can also be configured for retrofitting with tulips of conventional spinal support systems that are not "extension ready."

Figure 8:
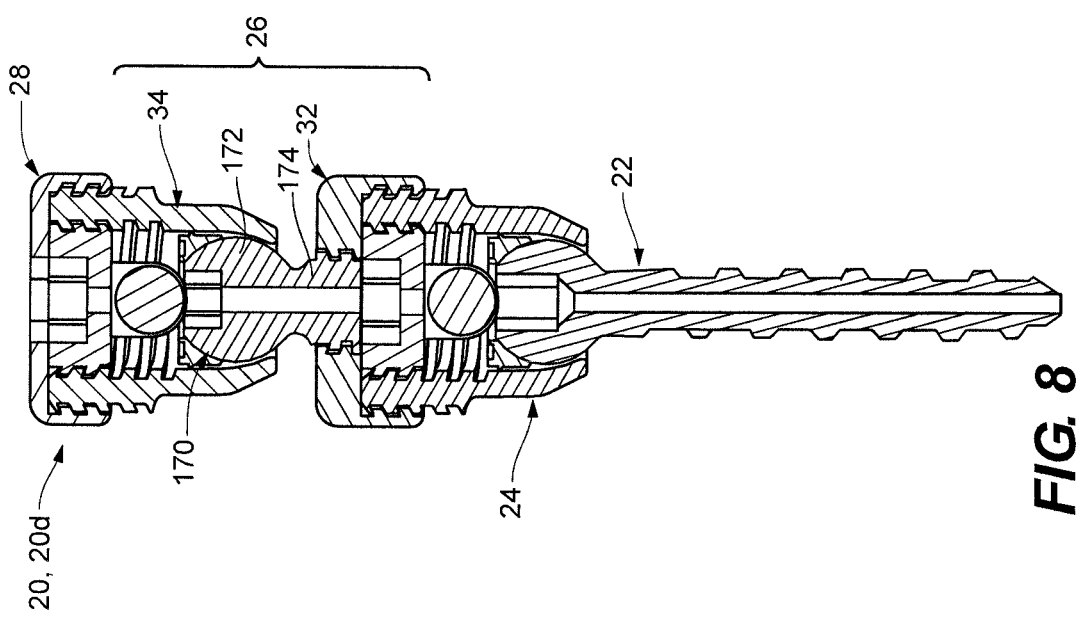
Figure 13:
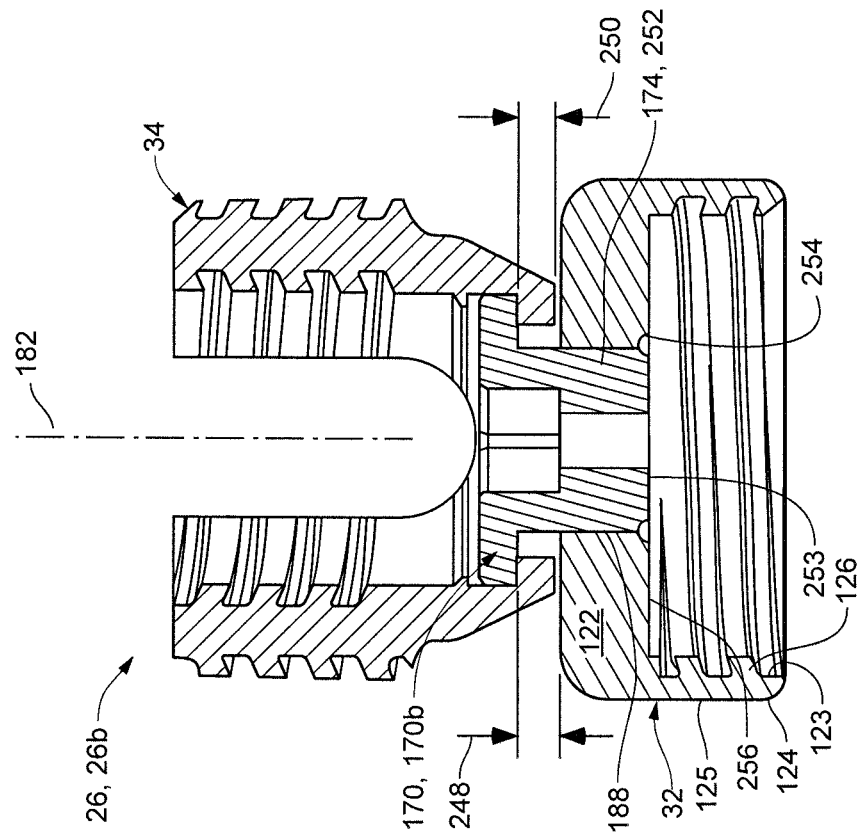
FIGS. 12 and 13 are sectional views depicting assembly of an extension sub-assembly having a welded pivot member according to an embodiment of the disclosure.
Figure 12:
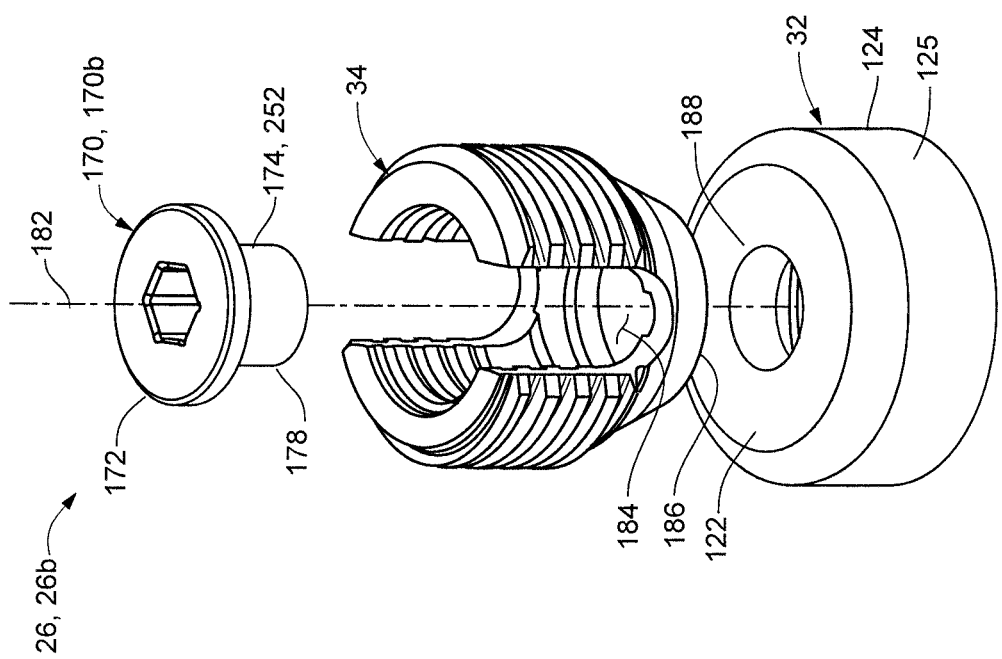

Referring to FIG. 8, an extensible spinal support system 20*d* is depicted according to an embodiment of the disclosure. As depicted the extensible spinal support system 20*d* includes many of the same components and attributes as the extensible spinal support system 20*a*, which are indicated with same numbered referenced characters. While components and attributes of the extensible spinal support system 20*a* are presented in the extensible spinal support system 20*d*, such components and attributes are not limiting. That is, the extensible spinal support system 20*d* may implement various aspects of the extensible spinal support systems 20*b* and 20*c* as well, which one of skill in the spinal support arts recognizes in view of this disclosure.

For the extensible spinal support system 20*d*, the head portion 172 of the pivot member 170*d* is spherical, and the extension rod receptacle 34 is configured as discussed above for the base rod receptacle 24. By this arrangement, the pivot member 170 and the extension rod receptacle 34 are configured for polyaxial rotation of the extension rod receptacle 34 about the head portion 172 of the pivot member 170.

Figure 9:
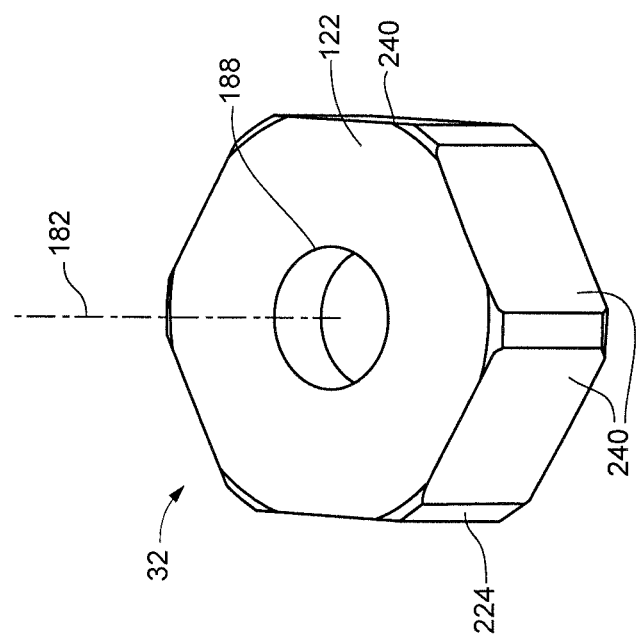
FIG. 9 is a perspective view of a platform of an extensible spinal support system with exterior wrench flats according to an embodiment of the disclosure.

Referring to FIG. 9, the skirt portion 124 of the base portion 34 is depicted with flats 240 according to an embodiment of the disclosure. The flats 240 are parallel to the pivot axis 182 and may be implemented with any of the depicted or contemplated embodiments. The embodiment of FIG. 9 depicts a total of six flats 240. By way of non-limiting example, the number of flats 240 may range from four to twelve. In some embodiments, the skirt portion 124 defines two flats 240 that are diametrically opposed. In some embodiments, the skirt portion 124 defines four flats 240 that are distributed as two diametrically opposed pairs that are rotationally offset at 90 degrees with respect to each other.

Referring to FIGS. 10 through 17, assembly of various extension subassemblies 26 are depicted according to embodiments of the disclosure. In FIGS. 10 through 17, the extension subassemblies and their associated pivot members are referred to collectively and generically by reference characters 26 and 170, respectively, and specifically by the reference characters 26 and 170 followed by a letter suffix (e.g., extension subassembly 26a and the associated pivot member 170a). Several components and attributes are common to all extension subassemblies 26, which are indicated with same numbered reference characters.

For the extension subassembly 26a (FIGS. 10 and 11), the pivot member 170a defines exterior shaft threads 176 formed on an exterior surface 178 of the shaft portion 174. The center hole 188 of the mounting platform 122 includes internal threads 192 for mating with the exterior shaft threads 176. In some embodiments, the pivot member 170a includes a stop 242, such as a shoulder 244 having a diameter 246 that is greater than the diameter of the exterior shaft threads 176. The stop 242 cooperates with the head portion 172 to define an axial gap dimension 248 that is greater than an axial thickness 250 of the internal flange 194.

In assembly, the pivot member 170a is inserted through the extension rod receptacle 34 and into the opening 184 so that the shaft portion 174 extends from the distal end 186 of the extension rod receptacle 34 and the head portion 172 of the pivot member 170a is within the extension rod receptacle 34. The shaft portion 174 of the pivot member 170a and the center hole 188 of the mounting platform 122 of the base portion 32a are then aligned and the exterior shaft threads 176 of the shaft portion 174 threaded into the internal threads 192 of the center hole 188. In some embodiments, the pivot member 170a is threaded into the center hole 188 until the stop 242 is firmly seated against the platform 122 over the mouth of the center hole 188 to define the axial gap dimension 248. Alternatively, the pivot member 170a may otherwise engage the base portion 32a in a manner that causes the pivot member 170a to stop within the center hole 188; for example, the threads 176 may cease at a point on the pivot shaft 174 that provides the desired axial gap dimension 248. Having secured the pivot member 170a to the mounting platform 122, the extension rod receptacle 34 is coupled to the base portion 32.

For the extension subassembly 26b (FIGS. 12 and 13), the shaft portion 174 of the pivot member 170b is a right cylinder 252, defining a smooth exterior surface 178. The center hole 188 of the mounting platform 122 is also right cylindrical, and may be dimensioned to provide a close sliding fit with the shaft portion 174. In some embodiments, the pivot member 170b includes a stop (not depicted) akin to pivot member 170a.

In assembly, the pivot member 170b is inserted through the extension rod receptacle 34 and into the opening 184 so that the shaft portion 174 extends from the distal end 186 of the extension rod receptacle 34 and the head portion 172 of the pivot member 170b is within the extension rod receptacle 34. The shaft portion 174 of the pivot member 170b and the center hole 188 of the mounting platform 122 of the base portion 32 are then aligned and the shaft portion 174 positioned within the center hole 188 to so that the axial gap dimension 248 is defined between the head portion 172 and the mounting platform 122. In some embodiments, the pivot member 170a is threaded into the center hole 188 until the stop 242 is firmly seated against the platform 122 over the mouth of the center hole 188, thereby defining the axial gap dimension 248. In some embodiments, the length of the shaft portion 174 is dimensioned to provide the desired axial gap dimension 248 when a distal end 253 of the shaft portion 174 is flush with a distal face 256 of the platform 122.

With the pivot member 170b positioned in the center hole 188 to define the axial gap dimension 248 greater than the axial thickness 250 of the internal flange 194, the pivot member 170b is secured to the platform 122. In the depicted embodiment, the distal end 253 of the pivot member 170b is welded to the distal face 256 of the mounting platform 122 to form a weld 254 at the perimeter of the center hole 188. The weld 254 may be continuous, a stitch weld, or a tack weld. The welding operation may be performed with welding techniques available to the artisan, including but not limited to electron beam welding. Alternatively, instead of welding, the pivot member 170b may be secured by other bonding or fusion techniques, such as brazing, soldering, or gluing. Upon securing the pivot member 170b to the base portion 32, the internal flange 294 of the extension rod receptacle 34, being captured between the head portion 172 and the mounting platform 122, is coupled to the base portion 32.

For the extension subassembly 26c (FIGS. 14 and 15), the shaft portion 174 of the pivot member 170c is also the right cylinder 252, defining the smooth exterior surface 178. The center hole 188 of the mounting platform 122 is also right cylindrical, and may be dimensioned to provide a close sliding fit with the shaft portion 174. Similar to pivot members 170a and 170c, the pivot member 170c may include the stop 242 such as the shoulder 244 with diameter 246, the diameter 246 being greater than the diameter of the center hole 188. As with the subassemblies 26a and 26b, the stop 242 of the subassembly 26c cooperates with the head portion 172 to define an axial gap dimension 248 that is greater than an axial thickness 250 of the internal flange 194. The distal face 256 of the mounting platform 122 may define a recessed lead in 258 that surrounds the center hole 188.

In assembly, the pivot member 170c is inserted through the extension rod receptacle 34 and into the opening 184 so that the shaft portion 174 extends from the distal end 186 of the extension rod receptacle 34 and the head portion 172 of the pivot member 170c is within the extension rod receptacle 34. The shaft portion 174 of the pivot member 170c and the center hole 188 of the mounting platform 122 of the base portion 32 are then aligned and the shaft portion 174 positioned within the center hole 188 so that the axial gap dimension 248 is defined between the head portion 172 and the mounting platform 122. In some embodiments, the pivot member 170c is inserted into the center hole 188 until the stop 242 registers against the platform 122 over the mouth of the center hole 188, thereby defining the axial gap dimension 248. In some embodiments, the length of the shaft portion 174 is dimensioned to provide the desired axial gap dimension 248 when the distal end 253 is flush with the distal face 256 of the platform 122.

With the pivot member 170c positioned in the center hole 188 to define the axial gap dimension 248 greater than the axial thickness 250 of the internal flange 194, the pivot member 170c is secured to the platform 122 by a swaging process. The swaging process deforms the distal end 253 of the shaft portion 174 into the recessed lead in 258. In this way, the mounting platform 122 is swaged between the stop 242 and the deformed distal end 253 of the pivot member 170c, akin to a rivet. The internal flange 294 is captured between the head portion 172 of the pivot member 170c and the mounting platform 122 of the base portion 32, thereby coupling the extension rod receptacle 34 to the base portion 32.

The depictions of FIGS. 10 through 15 present base portions 32 akin to base portion 32a, i.e., without an integral set screw portion. However, the assembly techniques for the subassemblies 26 described above are readily implemented for base portions 32 that include the set screw portion 228 integral therewith, akin to base portions 32b and 32c. The embodiments of FIGS. 6 and 7 depict the threaded pivot member 170a in combination with the integral set screw portion 228. The embodiments of FIGS. 16 and 17 depict the pivot members 170b and 170c with longer shaft portions 174 having distal ends 253 that reach the distal faces 257 of the integral set screw portions 228. The weld 254 (FIG. 16) and the recessed lead in 258 (FIG. 17) are formed on the distal faces 257 of the integral set screw portion 228. Accordingly, the subassemblies 26 may be fabricated with any of the base portions 32 described and depicted herein.

For the various subassemblies 26, because the axial gap dimension 248 is greater than the axial thickness 250 of the internal flange 194, monoaxial rotation of the extension rod receptacle 34 about the pivot axis 182 is achieved. That is, the internal flange 194, though effectively captured between the head portion 172 of the pivot member 170 and the base portion 32 of the extension subassembly 26, can be rotated about the pivot axis 182. In the depicted embodiment, movement of the of the extension rod receptacle 34 relative to the base portion 32 is effectively limited substantially to rotation about the pivot axis 182, i.e., a "monoaxial" rotation.

For the subassemblies 26 of FIGS. 10-15, because of the exterior threads 96 on the side wall 82 of the base rod receptacle 24, the extension rod receptacle 34 can be mounted to the base rod receptacle 24. That is, the extension subassemblies 26 of FIGS. 10-15 can be mounted directly to the exterior threads 96 of the base rod receptacle 24. For the subassemblies 26 of FIGS. 16 and 17, the extension rod receptacle 34 can be mounted to the interior threads 94 of the base rod receptacle 24, without need for exterior threads on the sidewall 82. Accordingly, because of the various subassemblies 26, the base rod receptacle 24 is referred to as "extension ready."

For the pre-assembled extension subassemblies 26 of FIGS. 10-15, the base portion 32 is aligned with the base rod receptacle 24 and the interior threads 126 of the skirt portion 124 of the base portion 32 threaded over the exterior threads 96 of the base rod receptacle 24. For the pre-assembled extension subassemblies 26 of FIGS. 16 and 17, the base portion 32 is aligned with the base rod receptacle 24 and both the interior threads 126 of the skirt portion 124 and the exterior threads external threads 232 of the set screw portion 228 are threadably engage with the exterior threads 96 of the base rod receptacle 24 and the internal threads 192 of the center hole 188, respectively. For the subassemblies 26, because the pivot member 170 is in fixed relationship with the base portion 32, the base portion 32 may be drawn tight against the proximal end 92 of the base rod receptacle 24 by with a driver inserted in the socket of the pivot member 170. The extension rod receptacle 34 may be rotated to a desired angular orientation about the pivot axis 182. The extension spinal support rod 38 is inserted into the extension rod receptacle 34, extending laterally through the diametrically opposed slots 148. The extension set screw 44 or, alternatively, the set screw portion 228, is threadably engaged with the interior threads 154 of the side wall 142 and tightened. When the set screw 44 is tightened against the extension spinal support rod 38, the extension rod receptacle 34 is drawn in the proximal direction (upward in FIG. 2) so that the internal flange 194 is drawn tight against the head portion 172, thereby locking the extension rod receptacle 34 in place and in a fixed rotational orientation relative to the head portion 172.

In some embodiments, in the absence of the extension subassembly 26, the cap 28 can be mounted to the exterior threads 96 of the base rod receptacle 24. Functionally, this arrangement provides support against outward lateral deflections (splaying) of the wall segments 90 would otherwise be provided by the skirt portion 124 of the mounting platform 122 of the extension subassembly 26. Various reinforcement caps 28 that can be implemented with either the base rod receptacle 24 or the extension rod receptacle 34 are described below attendant to FIGS. 25-32.

Similar to the extensible spinal support system 20a of FIG. 2, the extensible spinal support systems 20b and 20c of FIGS. 6 and 7 may be mounted to a previously implanted extension ready base assembly without need for removing or otherwise releasing the base spinal support rod 36. The base portions 32b and 32c of the extension subassemblies 26b and 26c may be mounted to the extension ready base assembly 21 of FIG. 1 instead of the set screw 42, the base portions 32b and 32c serving as a cap for securing the base spinal rod 36 to the base rod receptacle 24. The extension rod receptacle 34 can later be mounted directly to the center hole 188 of the mounting platform 122 of the base portion 32b with the pivot member 170a, thereby leaving the arrangement of the base rod receptacle 24 the base portions 32b, 32c and the base spinal support rod 36 intact. Accordingly, the base rod receptacle 24 in combination with the base portions 32b or 32c is also referred to as "extension ready." In such an embodiment, the extension subassemblies 26b and 26c are not pre-assembled, but instead assembled on the existing base portion 32b, 32c, being built up from the mounting platform 122 as described above.

Figure 18:
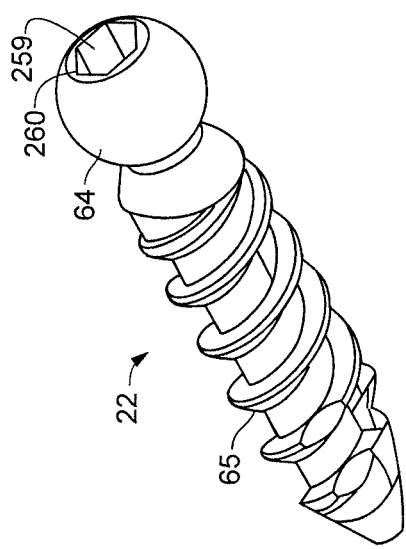
FIG. 18 is a perspective view of the pedicle screw of FIGS. 1 and 2 according to an embodiment of the disclosure.
Figure 18B:
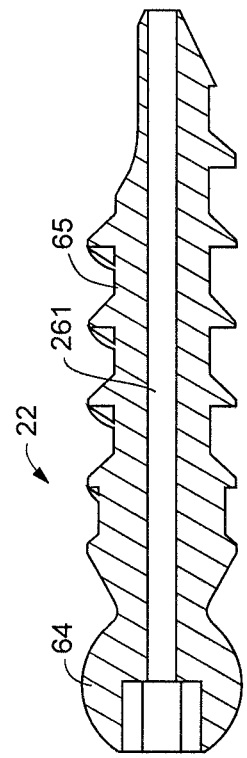
FIG. 18B is a sectional view of the pedicle screw at plane B-B of FIG. 18 according to an embodiment of the disclosure.
Figure 18A:
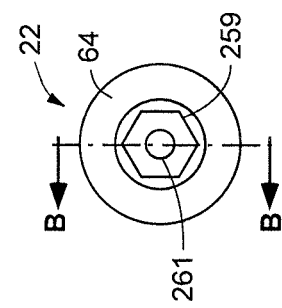
FIG. 18A is a top axial view of the pedicle screw of FIG. 18 according to an embodiment of the disclosure.

Referring to FIGS. 18 through 18B, the pedicle screw 22 is depicted in isolation in an embodiment of the disclosure. In addition to the components and attributes discussed above, the pedicle screw 22 may define a socket 259 in the head portion 64, accessible from a proximal end 260 of the pedicle screw 22. The threaded shaft portion 65 may be double threaded as depicted. In some embodiments, a center passage 261 extends through the head portion 64 and threaded shaft portion 65. In the depicted embodiment, the socket 259 is hexagonal, but other geometries, such as a square, rectangle, cross, or star pattern may be utilized.

Functionally, the socket 259 accommodates driving of the pedicle screw 22 with an appropriate mating wrench (e.g., hexagonal wrench for the depicted embodiment, or a square bit, rectangular bit, cross (PHILLIPS) bit, or star (TORR®) bit as appropriate). The center passage 261 may be sized, for example, to accommodate sliding passage of a KIRSCHNER wire or a larger diameter rod.

Referring to FIGS. 19 and 20A through 20C, a pedicle screw 22a is depicted according to an embodiment of the disclosure. The pedicle screw 22a includes some of the same components and attributes as pedicle screw 22, some of which are identified with same-labeled reference characters. In some embodiments, the pedicle screw 22a includes double threads 262a and 262b, referred to collectively and generically as threads or double threads 262. The pedicle screw 22a may define a self-tapping flute 264 at a distal end portion 265. In some embodiments, the threaded portion 65 of the pedicle screw 22a defines fenestrations 271 that are in fluid communication with the center passage 261. The pedicle screw 22a may define a depression 268 at a leading end 269 of each double thread 262a and 262b.

In some embodiments, the threads 262 that are terminated at the self-tapping flute 264 and include radiused or curved terminations 266 at the faces 267 of the self-tapping flute 264, thereby defining a convex profile that extends tangentially (i.e., in the θ-direction of the r-θ-z coordinate of FIG. 19) from proximate a root of the threads 262 at the faces 267 of the self-tapping flute 264 to a crest of the threads 262. In some embodiments, the curved terminations 266 define radii R. By way of non-limiting example, the radii may be within a range of: 100 to 400 micrometers inclusive; 100 to 300 micrometers inclusive; 150 to 300 micrometers inclusive; or 150 to 250 micrometers inclusive. Herein, a range that is said to be "inclusive" includes the endpoint values of the range as well as all values therebetween.

In some embodiments, a leading edge 263 of the flute 264 is rounded or otherwise dulled to blunt an otherwise sharp edge. The edges of the threaded shaft portion 65, such as corners at the crest of the threads 262, may be dulled to blunt an otherwise sharp edge. Techniques for producing the dulled edges include, for example, anodizing, surface polishing, or, in contrast, by surface roughening. Polishing techniques include tumbling the pedicle screw 22 in a granular or powder ceramic. Roughening techniques include sandblasting, wire brushing, laser-induced roughening, and etching. In some embodiments, the roughening techniques provide a surface roughness having an arithmetical mean deviation over the surfaces of the pedicle screw 22 that is in a range of 5 micrometers to 15 micrometers inclusive. The arithmetical mean deviation parameter, commonly referred to as "Ra" in the texturing arts, is described, for example, at Degarmo, et al., "Materials and Processes in Manufacturing," (9th ed.), p. 223, John Wiley & Sons (2003), ISBN 0-471-65653-4, the disclosure of which is hereby incorporated by reference herein except for express definitions contained therein.

Functionally, the curved terminations 266 reduce the sharpness of the threads 262 at the faces 267 of the self-tapping flute 264. With the curved terminations 266, the self-tapping flute 264 is still effective in tapping into bone tissue, but will not tend to cut soft tissue. Rather than cutting soft tissues, the curved terminations 266, as well as the dulled corners of the threads 262, tend to push soft tissue aside as opposed to slicing or tearing through the soft tissue. Such soft tissue includes blood vessels, which will tend to be deflected (instead of sliced) by the curved terminations 266. The fenestrations 271 promote the ingrowth of tissue into the pedicle screw 22a for a more secure mooring of the pedicle screw 22a within the bone over time.

The depression(s) 268 help compensate for the lack of a sharp cutting edge at the leading end 269 of the threads 262. In some embodiments, one depression 268 is formed at the leading end of each of the double threads 262a and 262b (depicted). The depressions 268 reduce the circumferential area of the pedicle screw 22a in the direction of rotation. For a given applied rotational force, the reduction in area produces an increase in the pressure applied by the pedicle screw 22a. The increased pressure augments penetration of the distal end portion 265 of the pedicle screw 22a through tissue without resort to sharp cutting edges, and also provides a relief that enables the tissue to flow over and around the leading end 269 of the thread 262.

Figure 21:
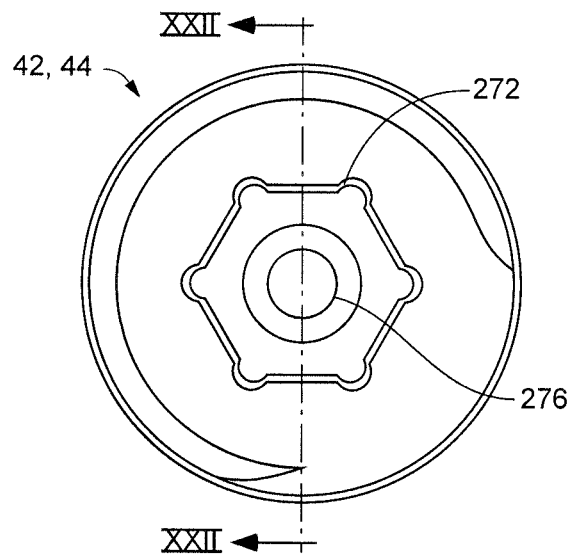
FIG. 21 is a top axial view of a set screw according to an embodiment of the disclosure.
Figure 22:
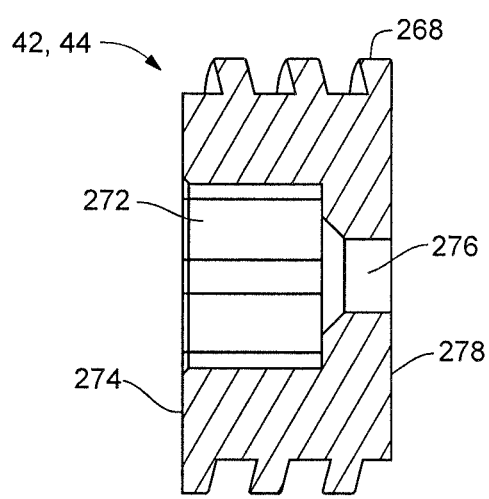
FIG. 22 is a section view of the set screw XXII-XXII of FIG. 21 at plane according to an embodiment of the disclosure.
Figure 23:
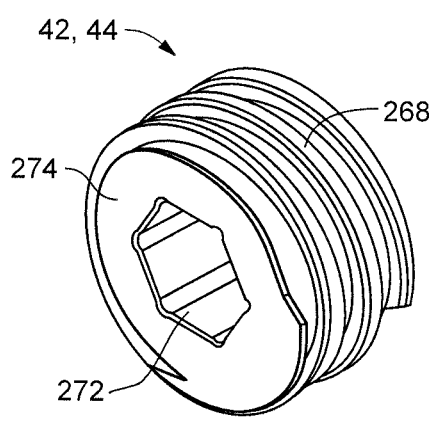
FIG. 23 is a perspective view of the set screw of FIG. 21 according to an embodiment of the disclosure.

Referring to FIGS. 21 through 23, the base or extension set screw 42, 44 is depicted in isolation in an embodiment of the disclosure. In the depicted embodiments, the base and extension set screws 42 and 44 are identical and are referred to collectively and generically as the "set screw 42, 44". The set screw 42, 44 includes exterior threads 270 that mate with the interior threads 94, 154 of the base or extension rod receptacle 24, 34. The set screw 42, 44 may define a socket 272, accessible from a proximal end 274 of the set screw 42, 44. In some embodiments, a center passage 276 extends from the socket 272 through a distal end 278 of the set screw 42, 44. In the depicted embodiment, the socket 272 is hexagonal, but other geometries, such as a square, rectangle, cross, or star pattern may be utilized.

Functionally, the socket 272 accommodates driving of the set screw 42, 44 with an appropriate mating wrench (e.g., hexagonal wrench for the depicted embodiment, or a square bit, rectangular bit, cross (PHILLIPS) bit, or star (TORX®) bit as appropriate). The center passage 276 may be sized, for example, to accommodate sliding passage of a KIRSCHNER wire or larger diameter rod.

Figure 24:
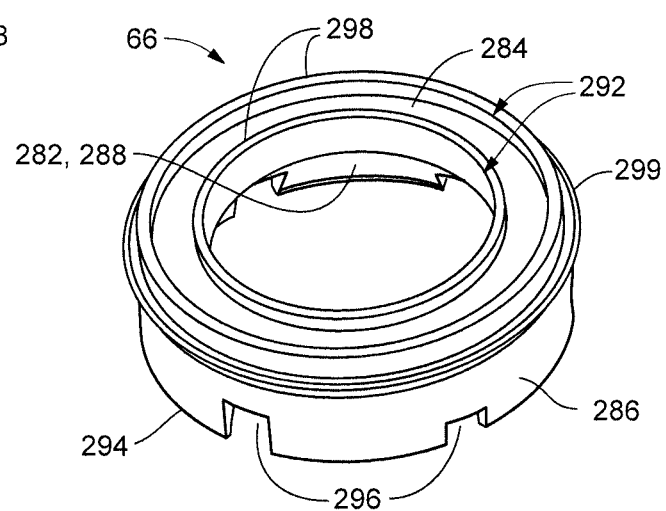
FIG. 24 is a perspective view of a lock ring according to an embodiment of the disclosure.

Referring to FIG. 24, the lock ring 66 is depicted in an embodiment of the disclosure. In some embodiments, the lock ring 66 includes a distal face 282 and a proximal face 284 separated by a perimeter portion 286. The distal face 282 may be convex and define a spherical profile 288. The proximal face 284 may include one or more malleable features 292 for engaging the base spinal support rod 36. The distal face 282 terminates at a distal edge 294 of the perimeter portion 286. In the depicted embodiment, a plurality of relief slots 296 are defined that are open at the distal edge 294 and extend axially into the perimeter portion 286. In some embodiments, the one or more malleable features 292 are plastically deformable. The one or more malleable features 292 may define a raised ridge 298, for example an annular ring as depicted in FIG. 24. In some embodiments, the lock ring 66 includes a radial detent 299 that extends radially outward from the perimeter portion 286.

Functionally, the convexity of the distal face 282 that accommodates and can slide over the spherical profile of the head portion 64 of the pedicle screw 22, thereby enabling the polyaxial movement of the base rod receptacle 24 relative to the head portion 64. The one or more malleable features 292 conform to the shape of the base spinal support rod 36 when the set screw 42 is tightened to secure the base spinal support rod 36 in place. The conformance of the malleable feature(s) 292 acts to grip the base spinal support rod 36, thereby inhibiting the base support rod 36 from rotating or sliding within the diametrically opposed slots 88 of the base rod receptacle 24. Upon tightening of the base set screw 42, the relief slots 296 enable the perimeter portion 286 to conform to the head portion 64 at the distal edge 294 for more effective gripping of the head portion 64 of the pedicle screw 22. The conformance of the malleable feature(s) 292 and perimeter portion 286 act to secure and inhibit movement between the head portion 64, the base spinal support rod 36, and the base rod receptacle 24. The radial detent 299 may interface with internal features 297 (FIG. 3) within the base rod receptacle 24, such as an internal inset flange (depicted) or optionally a groove (not depicted). The internal features 297 restrains the proximal face 284 from deflecting proximally (upward in FIGS. 2 and 3) when the lock ring 66 is deformed under the clamping force between the base spinal support rod 36 and the head portion 64, thereby maintaining gripping contact between the head portion 64 and the proximal face 284 of the lock ring 66.

Figure 25:
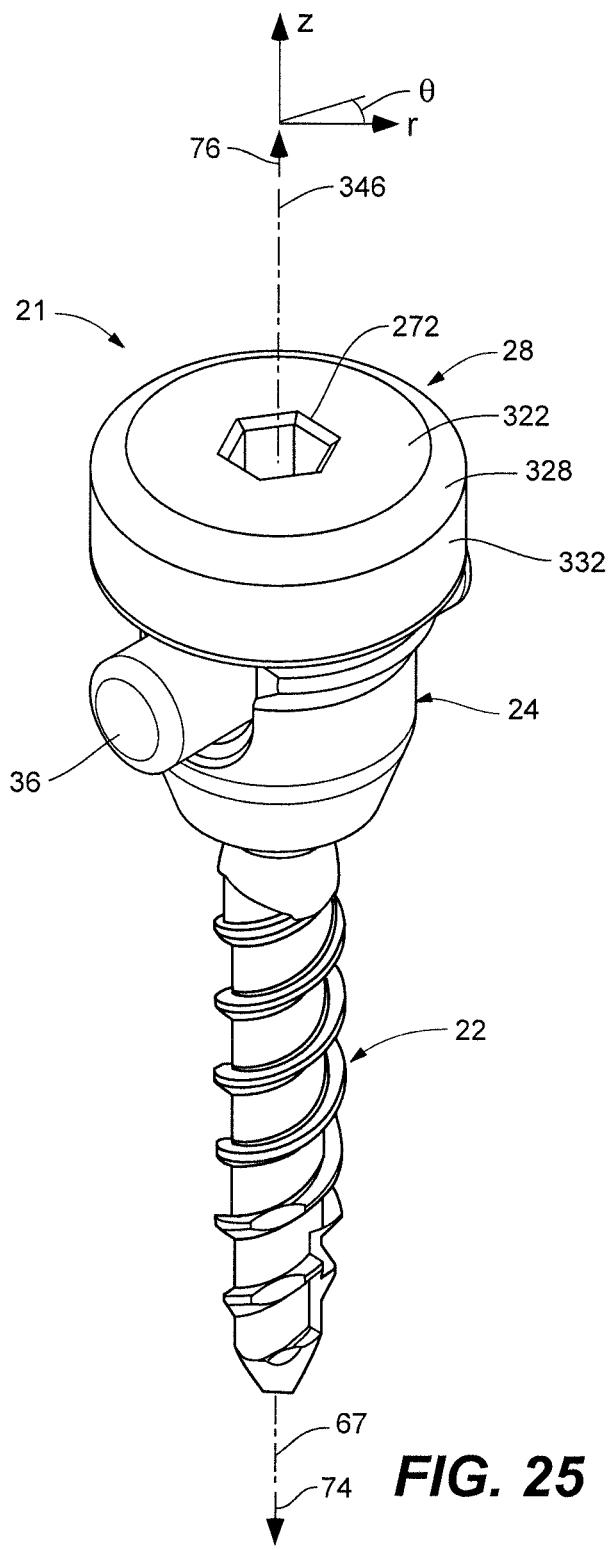
FIG. 25 is an upper perspective view of a spinal support system according to an embodiment of the disclosure.
Figure 26:
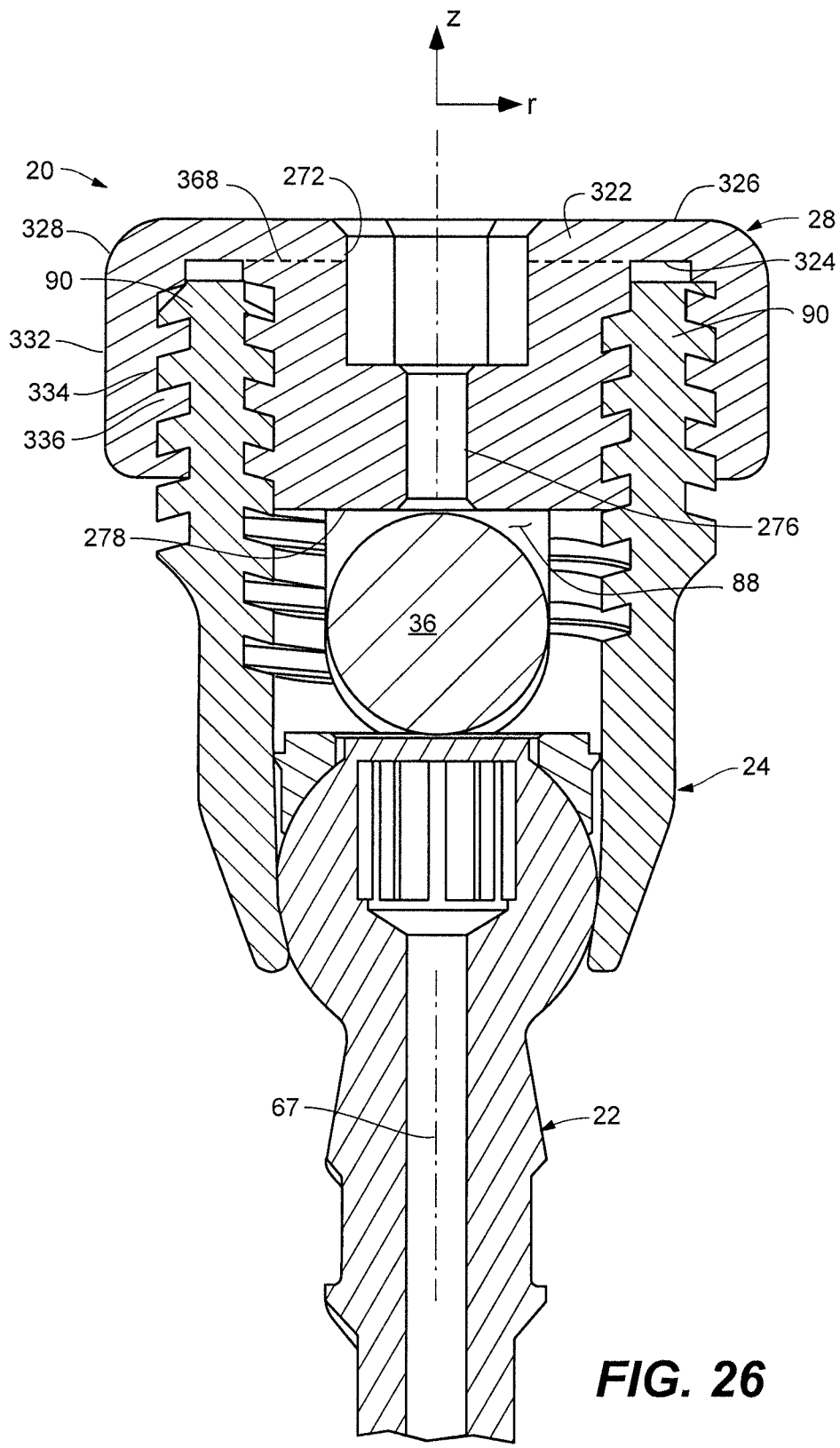
FIG. 26 is a partial sectional view of the spinal support system of FIG. 25 according to an embodiment of the disclosure.
Figure 27:
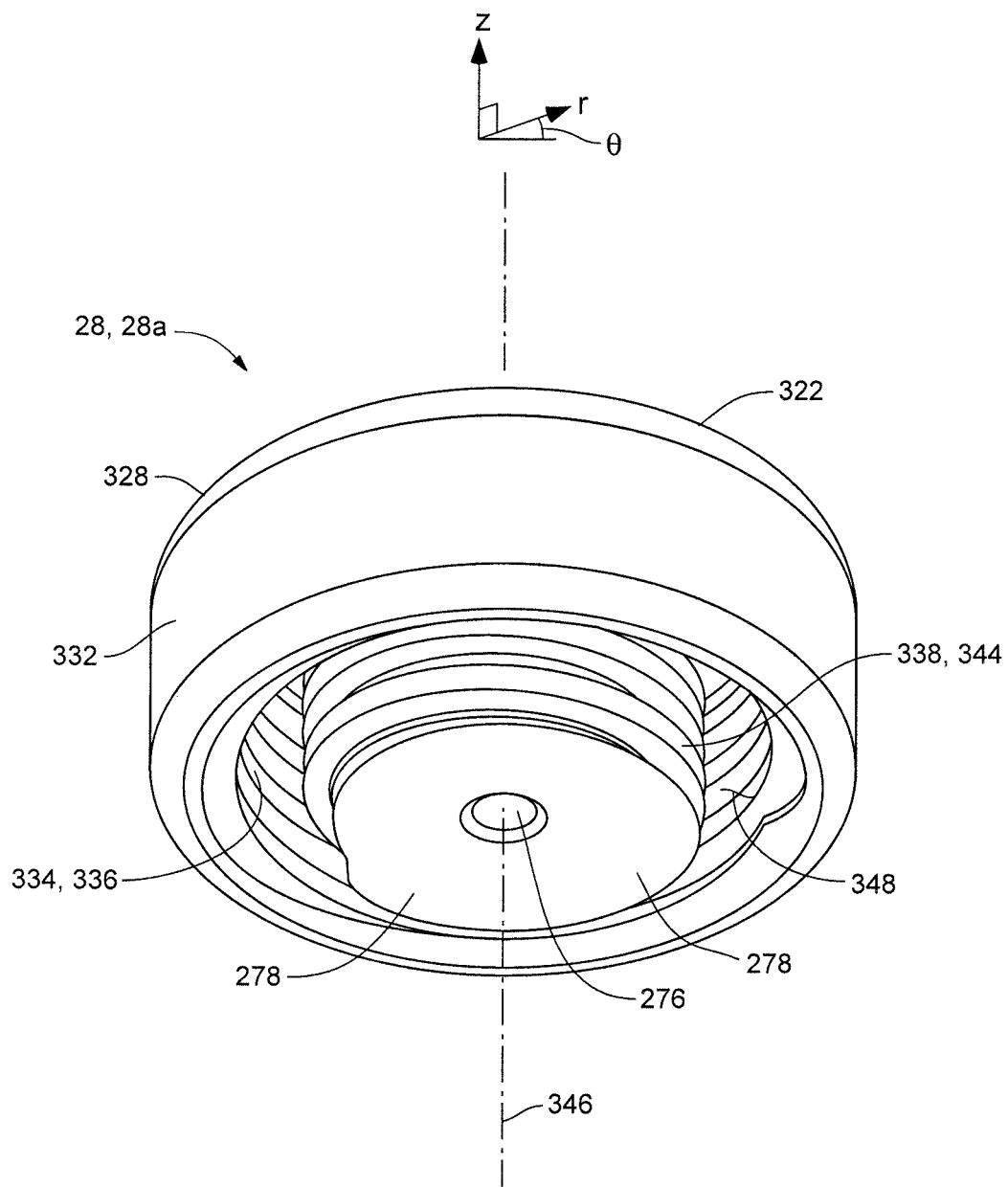
FIG. 27 is a lower perspective view of a reinforcement cap according to an embodiment of the disclosure.
Figure 28:
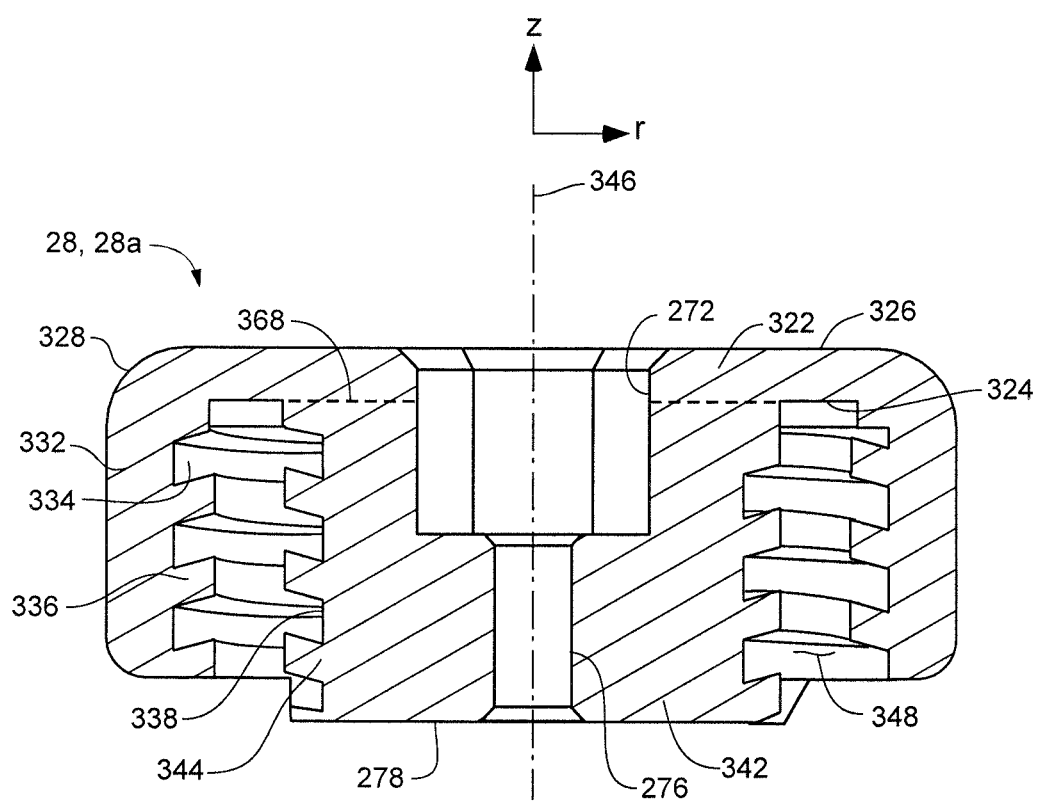
FIG. 28 is a sectional view of the reinforcement cap of FIG. 27 according to an embodiment of the disclosure.

Referring to FIGS. 25 and 26, the extension ready base assembly 21 is depicted with the reinforcement cap 28 coupled to the base rod receptacle 24. Referring to FIGS. 27 and 28, a reinforcement cap 28a is depicted according to an embodiment of the disclosure. Herein, various reinforcement caps are presented and referred to collectively and generically by reference character 28, and specifically by the reference character 28 followed by a letter suffix (e.g., reinforcement cap 28a). The reinforcement cap 28a includes a platform portion 322 including a distal face 324 and a proximal face 326 separated by a perimeter portion 328 (FIGS. 26, 27, and 28). A skirt portion 332 extends from the distal face 324 of the platform portion 322 portion, the skirt portion 332 including an interior surface 334, at least a portion of which includes interior threads 336 formed thereon. A set screw portion 342 extends from the distal face 324 of the platform portion 322, the set screw portion 342 being surrounded by the skirt portion 332 and including an exterior surface 338 that faces radially outward. At least a portion of the exterior surface 338 includes exterior threads 344 formed thereon. The set screw portion 342 defines a rotation axis 346 about which the set screw portion 342 and the skirt portion 332 are concentric. An annular gap 348 is defined between the exterior threads 344 of the set screw portion 342 and the interior threads 336 of the skirt portion 332.

The reinforcement cap 28a may define a socket 272 accessible from the proximal face 326 of the cap 28a. In the depicted embodiment, the socket 272 is hexagonal, but other geometries, such as a square, rectangle, octagon, cross, or star pattern may be utilized. In some embodiments, a center passage 276 extends from the socket 272 through a distal end 278 of the set screw portion 342.

Figure 29:
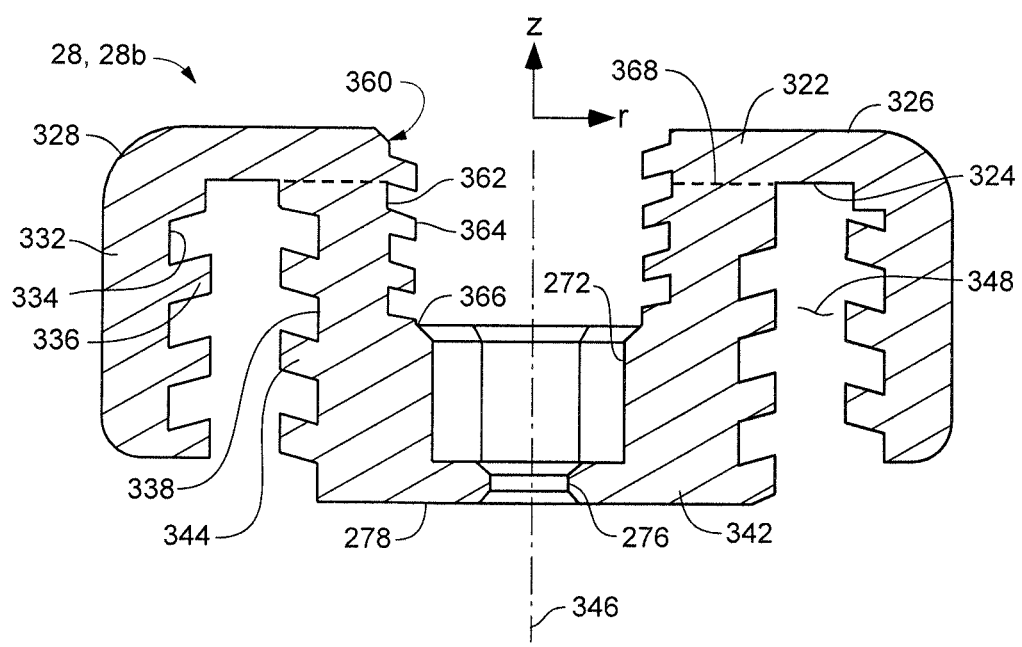
FIG. 29 is a sectional view of a reinforcement cap having a tapped center hole according to an embodiment of the disclosure.

Referring to FIG. 29, a reinforcement cap 28b modified to define a tapped center hole 360 is depicted according to an embodiment of the disclosure. The reinforcement cap 28b includes many of the same components and attributes as the reinforcement cap 28a, which are indicated with same-numbered numerical characters. The tapped center hole 360 is characterized as having an inner wall 362 on which threads 364 are formed, and a bottom surface 366. The socket 272 extends distally from the bottom surface 366.

Figure 30:
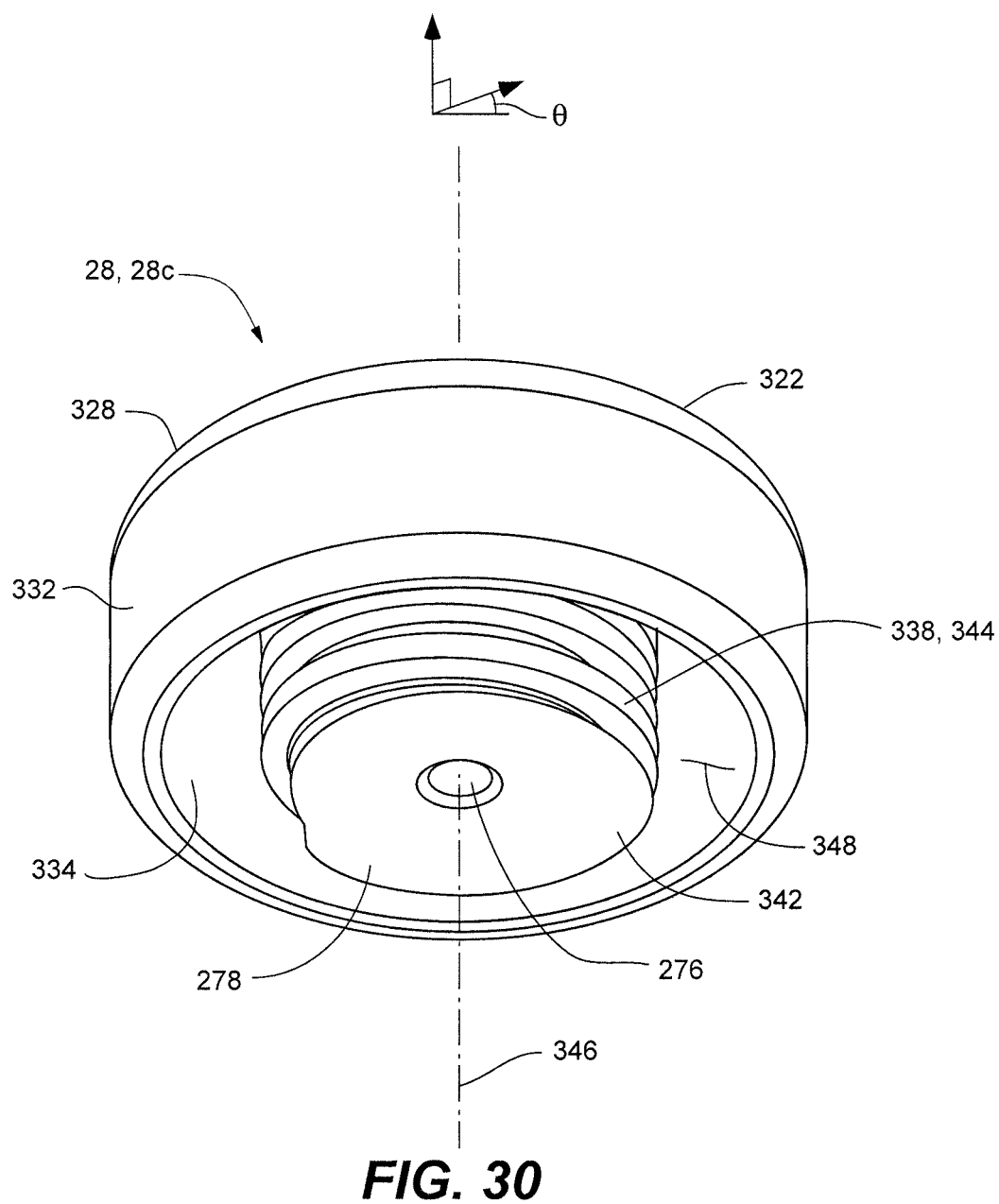
FIG. 30 is a lower perspective view of a reinforcement cap according to an embodiment of the disclosure.
Figure 31:
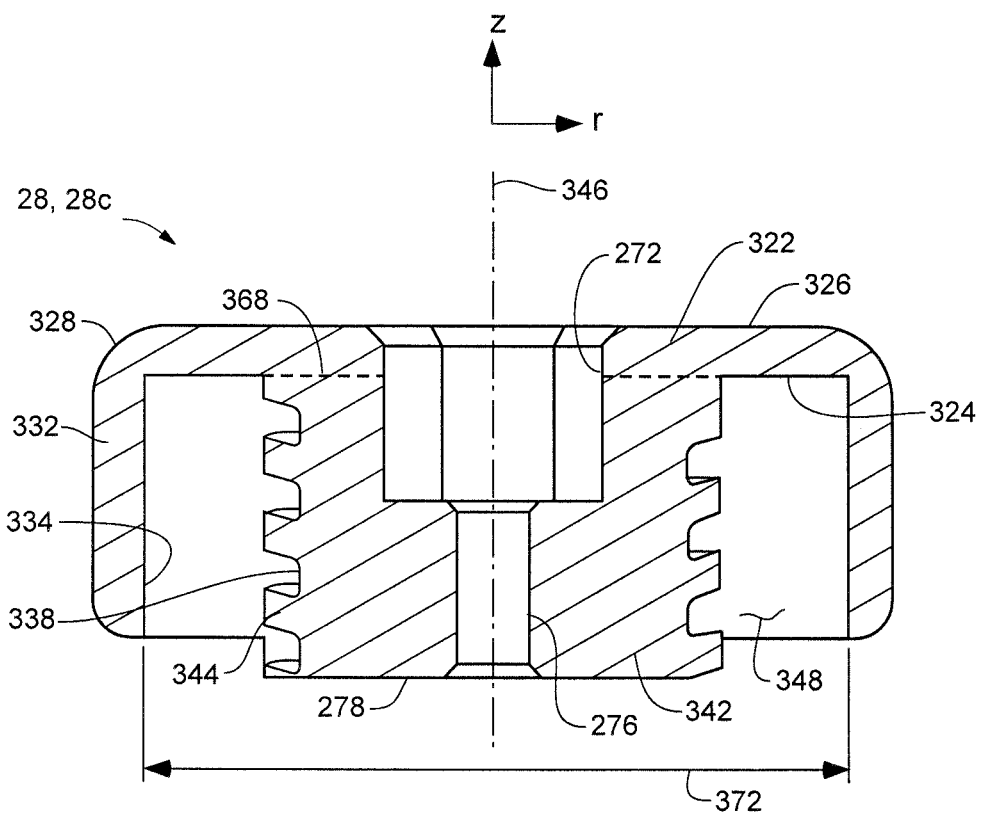
FIG. 31 is a sectional view of the reinforcement cap of FIG. 30 according to an embodiment of the disclosure.

Referring to FIGS. 30 and 31, a reinforcement cap 28c is depicted according to an embodiment of the disclosure. The reinforcement cap 28c includes many of the same components and attributes as the reinforcement cap 28a and 28b, which are indicated with same-numbered reference characters. A distinction of the reinforcement cap 28c is that the skirt portion 332 does not include interior threads, such that the skirt portion 332 slidingly engages and rotates about the exterior threads 96 of the base rod receptacle 24 but does not threadably engage the exterior threads 96. Accordingly, the reinforcement cap 28c threadably engages only with the interior threads 94 of the side wall 82. In some embodiments, the skirt portion 332 may define an inner diameter 372 that slides over the exterior threads 96 with a close, sliding fit.

Figure 32:
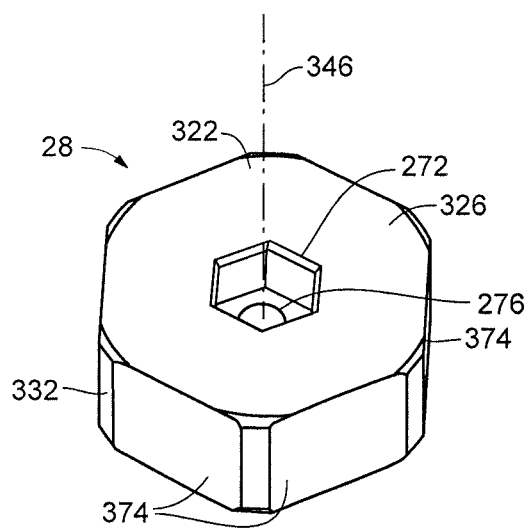
FIG. 32 is an upper perspective view of a reinforcement cap with flats according to an embodiment of the disclosure.

Referring to FIG. 32, the skirt portion 332 of the reinforcement cap 28 is depicted with flats 374 according to an embodiment of the disclosure. The flats 374 extend parallel to the rotation axis 346 and may be implemented with any of the depicted or contemplated reinforcement caps 28. The embodiment of FIG. 32 depicts a total of six flats 374 as a non-limiting example. In some embodiments the number of flats 374 is in a range of six to twelve inclusive. In some embodiments, the skirt portion 332 defines two flats 374 that are diametrically opposed. In some embodiments, the skirt portion 332 defines four flats 374 that are distributed as two diametrically opposed pairs that are rotationally offset at 90 degrees with respect to each other.

Functionally, the interior threads 94 of the base rod receptacle 24 are configured to mate with the exterior threads 344 of the set screw portion 342 of the reinforcement cap 28. For the reinforcement caps 28a and 28b, the exterior threads 96 of the base rod receptacle 24 are configured to mate with the interior threads 336 of the skirt portion 332 of the reinforcement cap 28, 28b. The socket 272 accommodates driving of the reinforcement cap 28, 28b with an appropriate mating wrench (e.g., hexagonal wrench for the depicted embodiment, or a square bit, rectangular bit, cross (PHILLIPS) bit, or star (TORX®) bit as appropriate). The flats 374, when implemented, provide an alternative way to apply torsion to the reinforcement cap 28, for example by use of socket tool that slides over and engages the flats 374. The flats 374 can also be used in so-called rescue situations, providing alternative gripping surfaces for removal of components of the spinal support system 20. The center passage 276 may be sized, for example, to accommodate sliding passage of a KIRSCHNER wire or a guide rod.

The unitary or otherwise integral structure of the set screw portion 342 with the platform portion 322 and skirt portion 332 provides additional structural strength and integrity relative to a separate cap and set screw arrangement. For example, the spinal support system 20 provides greater resistance to lateral forces because the set screw portions 342 is integrated with the platform portion 322, establishing a shear stress at a junction 368 of the screw portion 342 and the platform portion 322 that provides additional resistance to deformation relative to an assembly where the cap and set screw are separate components. The added strength and structural integrity provided by the integrated arrangement of the reinforcement cap 28 may be advantageous for high torque and high stress applications, such as scoliosis correction.

Referring to FIGS. 33, 33A, 34, and 34A, threads defining a canted cantilever profile 450 and the advantage provided over conventional threaded arrangements are depicted and described according to embodiments of the disclosure. Conventional threaded arrangements 400, schematically depicted at FIGS. 33 and 33A, may include, for example, exterior threads 402 of a set screw 404 that are engaged with interior threads 406 of a wall segment 408 of a spinal rod receptacle 410 (akin to opposed wall segments 90 and 150 of the rod receptacles 24 and 34 of the extensible spinal support system 20). Both the set screw 404 and the wall segment 408 are concentric about a central axis 412 that defines the z-axis of a right-cylindrical coordinate system 424 having an axial coordinate z and a radial coordinate r. When the set screw 404 is tightened in the first direction 416 to set against a spinal support rod 415, a clamping force vector FC is generated, for which there is an equal and opposite force vector FC' in a second direction 418 that is opposite the first direction 416. The force vector FC' in turn generates reaction force vectors FR generated at contact interfaces 422 between the proximal faces of the exterior threads 402 of the set screw 404 and the distal faces of the interior threads 406 of the wall segment 408. The reaction forces FR generate an axial component FRZ and radial component FRR. Because of the standard shape of the threads 402 and 406, the radial components FRR generate a radial outward force FRO, i.e., away from the central axis 412.

For configurations such as the depicted extensible spinal support system 20, the wall segment 408 (e.g., wall segment 90 of the extensible spinal support system 20) is, in some embodiments, not supported by any structure other than resistance to bending at the base of the wall segment. In such embodiments, the wall segment 408 will tend to cause deflections δo that deflect radially outward in response to the radial outward force FRO. As the wall segment 408 deflects radially outward, the overlap between the threads 406 and 408 at the interfaces 422 is reduced, thereby weakening the coupling between the set screw 404 and the wall segment 408. The tighter the draw on the set screw 404, the greater the radial outward force FRO and the greater the deflection of the wall segment 408, further decreasing the overlap at the interfaces 422. Accordingly, as the torque requirements of the conventional set screw 404 are increased, the coupling between the set screw 404 and the wall segment 408 becomes more tenuous. Over time, creep stresses may cause the deflection of the wall segment 408 (splaying) and the attendant decrease in the overlap at the interfaces 422, causing the clamping force FC to reduce. This can cause loosening of the assembly and slippage of the resident spinal rod within the spinal rod receptacle 410. In some instances, torque requirements can cause the set screw 404 to slip within the spinal rod receptacle 410 during implantation.

Figure 34:
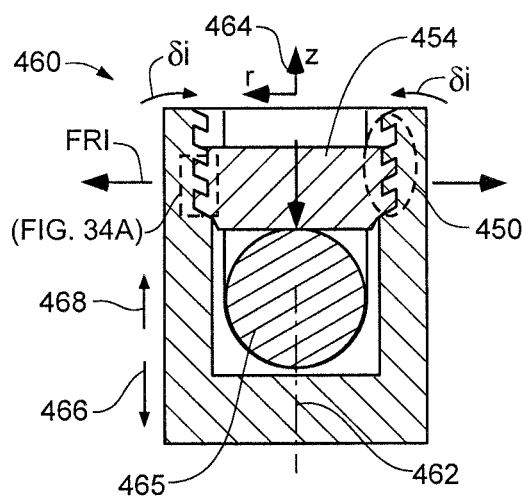
FIG. 34 is a sectional view of a rod receptacle in assembly having threads that define a canted cantilever profile according to an embodiment of the disclosure.
Figure 34A:
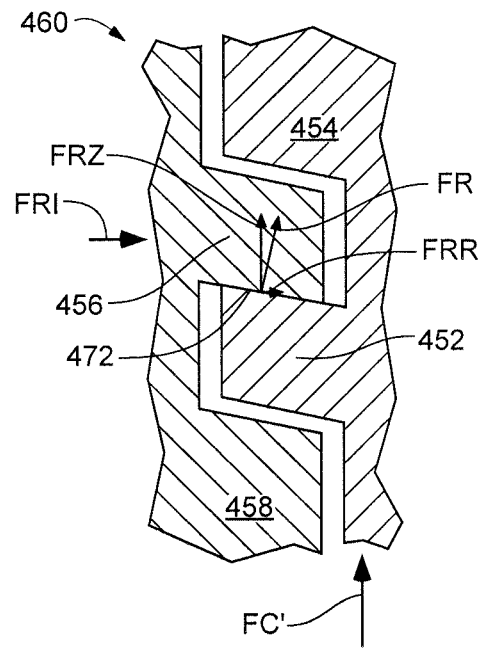
FIG. 34A is an enlarged, partial view of FIG. 34 according to an embodiment of the disclosure.

A remedy for the splaying and attendant slippage of the spinal rod is a threaded arrangement utilizing threads having the canted cantilever profile arrangement 450, as depicted at FIGS. 34 and 34A. The various threads 94, 96, 126, 154, 156, and 270 (FIGS. 2, 4, and 5) of the extensible spinal support system 20 may utilize a canted cantilever profile arrangement. The canted cantilever profile arrangement 450, schematically depicted at FIGS. 34 and 34A, may include, for example, exterior threads 452 of a set screw 454 that are engaged with interior threads 456 of a wall segment 458 of a spinal rod receptacle 460 (akin to opposed wall segments 90 and 150 of the rod receptacles 24 and 34 of the extensible spinal support system 20). Both the set screw 454 and the wall segment 458 are concentric about a central axis 462 that defines the z-axis of a right-cylindrical coordinate system 464 having an axial coordinate z and a radial coordinate r. When the set screw 454 is tightened a first direction 466 to set against a spinal support rod 465, the clamping force vector FC is generated, for which there is the equal and opposite force vector FC' in a second direction 468 that is opposite the first direction 466. The force vector FC' in turn generates reaction force vectors FR generated at contact interfaces 472 between the proximal faces of the exterior threads 452 of the set screw 454 and the distal faces of the interior threads 456 of the wall segment 458. The reaction forces FR generate an axial component FRZ and radial component FRR.

However, unlike the conventional threaded arrangements 400, the contact interfaces 472 of the canted cantilever profiles 450 are sloped radially inward (i.e., toward the central axis 462) in the first direction 466. By this arrangement, the radial component FRR is vectored inward, toward the central axis 462. The forces so generated will tend to cause deflections δi of the wall segment 458 that is radially inward in response to the radial inward force FRI. Because of the radial inward deflections δi, the wall segments 458 tend to be supported by the set screw 454. Accordingly, the coupling between the set screw 454 and the spinal rod receptacle 460 provided by the canted cantilever profile arrangement 450 is stronger and can provide a greater clamping force FC than can the conventional threaded arrangement 400 of spinal rod receptacle 410.

For the extensible spinal support system 20, the interior threads 94, 154 of the base and extension rod receptacle 24, 34 interact with the set screws 42, 44 in the manner described attendant to the canted cantilever profile arrangement 450 of FIGS. 34 and 34A. The exterior threads 96, 156 of the base and extension rod receptacle 24, 34 may also implement a canted cantilever arrangement (see, e.g., FIGS. 2, 4, and 5), but may be configured to generate different forces and deflections. For example, the exterior threads 96, 156 of the base and extension rod receptacle 24, 34 are sloped radially outward (i.e., away from the central axis 462) in the distal direction 74. By this arrangement, the radial components of the reaction forces at the interface of the exterior threads 96, 156 and the interior threads 126, 226 of the skirt portions 124, 224 is vectored outward, away from the center axis 67. The forces so generated will tend to cause the wall segments 90, 150 to deflect radially outward. Because of the radial outward deflections, the wall segments 90, 150 tend to be supported by the skirt portions 124, 224. The skirt portions 124, 224, being tangentially continuous, incurs a hoop stress that further counters the outward radial forces and limits splaying. The outward radial forces at the exterior threads 96, 156 also tend to counter and can be tailored to balance the inward radial forces FRI to further reduce overall radial deflection and deformation of the wall segments 90, 150.

Figure 33:
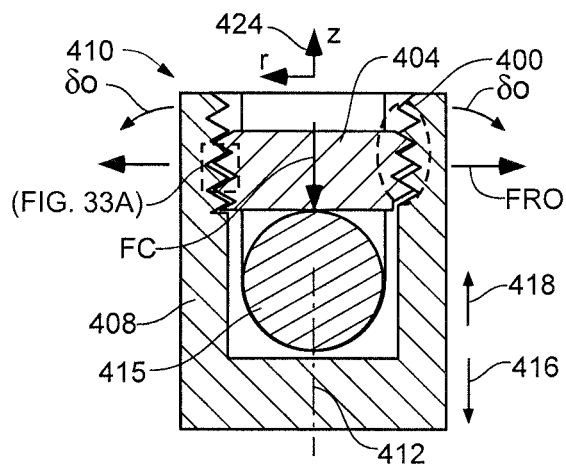
FIG. 33 is a sectional view of a conventional rod receptacle in assembly.
Figure 33A:
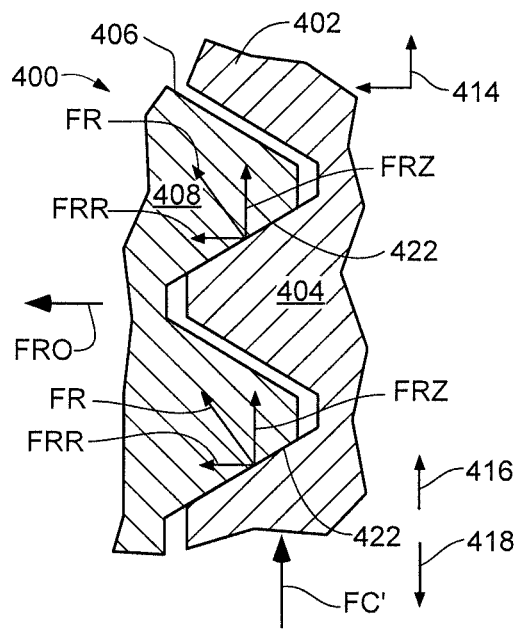
FIG. 33A is an enlarged, partial view of FIG. 33.

Alternatively, the exterior threads 96, 156 of the receptacles 24, 34 and the interior threads 126, 226 of the skirt portions 124, 224 may be of a conventional arrangement. Conventional threads, as described attendant to FIGS. 33 and 33A, provide radial outward forces that are subsequently supported by the skirt portions 124, 224 and as a counter to the radial inward force FRI, to prevent splaying.

Figure 35:
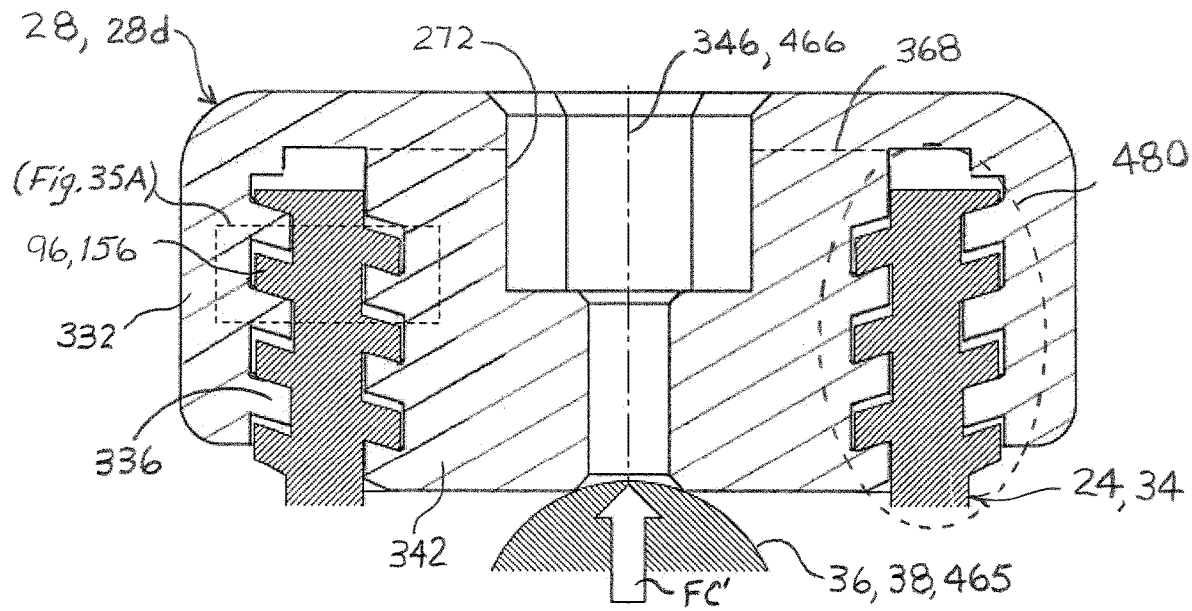
FIG. 35 is a partial sectional view of a rod receptacle in assembly having reversed canted cantilever threads according to an embodiment of the disclosure.
Figure 35A:
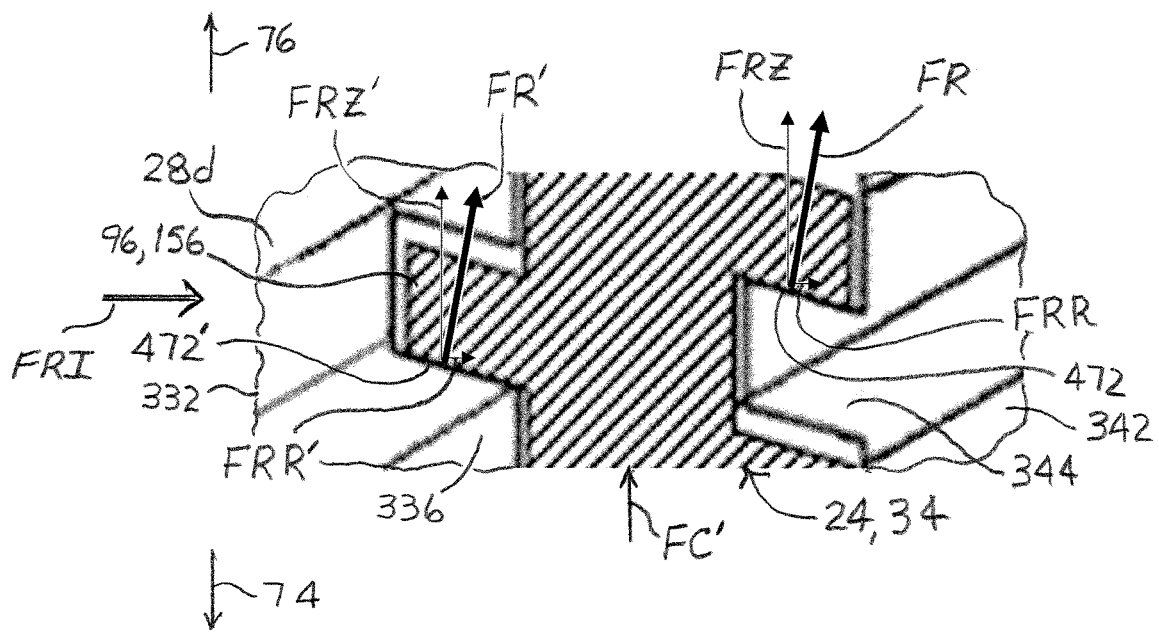
FIG. 35A is an enlarged, partial view of FIG. 35 according to an embodiment of the disclosure.

Referring to FIGS. 35 and 35A, a partial view of the extensible spinal support system 20 having a reinforcement cap 28d and rod receptacle 24, 34 that define a reverse canted cantilever profile 480 is depicted according to an embodiment of the disclosure. The reinforcement cap 28d includes many of the same components and attributes as the reinforcement caps 28a and 28b, as well as the reaction vectors of FIGS. 34 and 34A, all of which are indicated with same-numbered reference characters. A distinction of the FIGS. 35 and 35A embodiment is that the exterior threads 96, 156 of the receptacles 24, 34 are sloped radially outward (i.e., away from the rotation axis 346) in the proximal direction 76 instead of the distal direction 74, with the interior threads 336 of the skirt portion 332 of the reinforcement cap 28d being configured to mate therewith.

In FIG. 35A, the reaction force vector FR at the contact interface 472 and the components FRR and FRZ thereof are superimposed from FIG. 34A at the exterior threads 344 of the set screw portion 342 and the interior threads 94, 154 of the base or extension rod receptacle 24, 34. A reaction force vector FR' at a contact interface 472' and the components FRR' and FRZ' thereof are depicted at the interior threads 336 of the skirt portion 332 and the exterior threads 96, 156 of the base or extension rod receptacle 24, 34.

Functionally, by this arrangement, not only do the reaction force vectors FR at the contact interface 472 generate the radial component FRR vectored inward (i.e., toward the center axis 466), but so do the reaction force vectors FR' at the contact interfaces 472'. Accordingly, both the contact interfaces 472 and 472' contribute to the radial inward force FRI that opposes the splaying that may result from the setting of the set screw portion 342.

The depictions of FIGS. 35 and 35A illustrate the reinforcement cap 28d in assembly on the base or extension rod receptacle 24, 34. The same arrangement for the reverse canted cantilever profile 480 may be employed mutatis mutandis with the various base portions 32 in assembly with the rod receptacle 24, which one of ordinary skill in the pedicle screw and tulip arts understands in view of this disclosure.

Each of the additional figures and methods disclosed herein can be used separately, or in conjunction with other features and methods, to provide improved devices and methods for making and using the same. Therefore, combinations of features and methods disclosed herein may not be necessary to practice the disclosure in its broadest sense and are instead disclosed merely to particularly describe representative and preferred embodiments.

Various modifications to the embodiments may be apparent to one of skill in the art upon reading this disclosure. For example, persons of ordinary skill in the relevant arts will recognize that the various features described for the different embodiments can be suitably combined, un-combined, and re-combined with other features, alone, or in different combinations. Likewise, the various features described above should all be regarded as example embodiments, rather than limitations to the scope or spirit of the disclosure.

Persons of ordinary skill in the relevant arts will recognize that various embodiments can comprise fewer features than illustrated in any individual embodiment described above. The embodiments described herein are not meant to be an exhaustive presentation of the ways in which the various features may be combined. Accordingly, the embodiments are not mutually exclusive combinations of features; rather, the claims can comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

Unless indicated otherwise, references to "embodiment (s)", "disclosure", "present disclosure", "embodiment(s) of the disclosure", "disclosed embodiment(s)", and the like contained herein refer to the specification (text, including the claims, and figures) of this patent application that are not admitted prior art.

For purposes of interpreting the claims, it is expressly intended that the provisions of 35 U.S.C. 112(f) are not to be invoked unless the specific terms "means for" or "step for" are recited in the respective claim.

What is claimed is:

1. A vascular-safe pedicle screw, comprising:
a head portion;
a threaded shaft portion distal to said head portion and including threads that extend to a distal end portion of said threaded shaft portion; and
a self-tapping flute at the distal end portion of said threaded shaft portion, said self-tapping flute being recessed into said threaded shaft to define at least one terminated thread at a face of said self-tapping flute, wherein said at least one terminated thread is curved to define a convex profile that extends in a tangential direction from proximate a root of said at least one terminated thread at said face of said self-tapping flute to a crest of said at least one terminated thread, and wherein said distal end portion of said threaded shaft portion defines a depression at a leading end of said threads.

2. The vascular-safe pedicle screw of claim 1, wherein said convex profile defines a radius.

3. The vascular-safe pedicle screw of claim 1, wherein said threads are double threads.

4. The vascular-safe pedicle screw of claim 1, wherein said head portion and said threaded shaft portion define a central passage that passes therethrough.

5. The vascular-safe pedicle screw of claim 4, wherein said threaded portion defines a plurality of fenestrations that are in fluid communication with said central passage.

6. The vascular-safe pedicle screw of claim 1, wherein said depression extends in said tangential direction from a leading end of said threads.

7. The vascular safe pedicle screw of claim 6, wherein said depression defines a depth that extends orthogonal to a central axis of said vascular safe pedicle screw.

8. The vascular-safe pedicle screw of claim 1, wherein said threaded shaft portion includes dulled edges.

9. The vascular-safe pedicle screw of claim 8, wherein said dulled edges are polished.

10. The vascular-safe pedicle screw of claim 8, wherein said dulled edges are roughened.

11. The vascular-safe pedicle screw of claim 10, wherein said threaded shaft portion defines a surface roughness having arithmetical mean deviation that is in a range of 5 micrometers to 15 micrometers inclusive.

12. A spinal rod support system, comprising:
a pedicle screw, including:
a head portion;
a threaded shaft portion distal to said head portion and including threads that extend to a distal end portion of said threaded shaft portion;
a self-tapping flute at the distal end portion of said threaded shaft portion, said self-tapping flute being recessed into said threaded shaft to define terminations of said threads at a face of said self-tapping flute, said terminations defining a convex profile that extends in a tangential direction from a root to a crest of said threads at said face of said self-tapping flute; and
a depression defined at a leading end of said threads at said distal end portion of said threaded shaft portion;
a base rod receptacle coupled to said pedicle screw; and
an extension rod receptacle configured to couple to said base rod receptacle.

13. The spinal rod support system of claim 12, wherein said threaded shaft portion includes dulled edges.

14. The spinal rod support system of claim 12, comprising a base portion configured to threadably couple to said base rod receptacle, the base portion including a skirt portion that extends from a mounting platform, said mounting platform defining a center hole accessible from a proximal face of said mounting platform, said extension rod receptacle extending into said center hole.

15. The spinal rod support system of claim 14, wherein:
said base rod receptacle defines exterior threads;
said skirt portion of said base defines interior threads configured to mate with said exterior threads of said base rod receptacle.

16. The spinal rod support system of claim 15, comprising a reinforcement cap configured to couple to one of said base rod receptacle and said extension rod receptacle, said reinforcement cap including a set screw portion and a skirt portion, wherein:
said base rod receptacle defines interior threads;
said extension rod receptacle defines interior threads; and
said set screw portion of said reinforcement cap defines exterior threads configured to mate with either of said interior threads of said base rod receptacle or said interior threads of said extension rod receptacle.

17. The spinal rod support system of claim 16, wherein:
said extension rod receptacle defines exterior threads;
said skirt portion of said reinforcement cap defines interior threads configured to mate with either of said exterior threads of said base rod receptacle or said exterior threads of said extension rod receptacle.

18. The spinal rod support system of claim 17, wherein:
said interior threads of said base rod receptacle and said interior threads of said extension rod receptacle each define a first canted cantilever profile that extends radially inward and in a distal direction; and
said exterior threads of said base rod receptacle and said exterior threads of said extension rod receptacle each define a second canted cantilever profile that extends radially outward and in a proximal direction.

19. The spinal rod support system of claim 12, wherein said depression extends in said tangential direction from a leading end of said threads.

20. The spinal rod support system of claim 19, wherein said depression defines a depth that extends orthogonal to a central axis of said pedicle screw.

\* \* \* \* \*